United States Patent
Rüdlinger

(10) Patent No.: US 10,844,302 B2
(45) Date of Patent: Nov. 24, 2020

(54) THERMAL AND CHEMICAL UTILIZATION OF CARBONACEOUS MATERIALS, IN PARTICULAR FOR EMISSION-FREE GENERATION OF ENERGY

(71) Applicant: RV Lizenz AG, Cham (CH)

(72) Inventor: Mikael Rüdlinger, Cham (CH)

(73) Assignee: RV LIZENZ AG

( * ) Notice: Subject to any disclaimer, the term of this patent is extended or adjusted under 35 U.S.C. 154(b) by 0 days.

(21) Appl. No.: 16/567,326

(22) Filed: Sep. 11, 2019

(65) Prior Publication Data
US 2020/0002632 A1   Jan. 2, 2020

Related U.S. Application Data

(62) Division of application No. 13/509,883, filed as application No. PCT/EP2010/067847 on Nov. 19, 2010, now Pat. No. 10,450,520.

(30) Foreign Application Priority Data

Nov. 20, 2009 (EP) .................................... 09176684
Jan. 22, 2010 (EP) .................................... 10151473
(Continued)

(51) Int. Cl.
  *C10J 3/20* (2006.01)
  *C10J 3/40* (2006.01)
  (Continued)

(52) U.S. Cl.
  CPC .............. *C10J 3/66* (2013.01); *C07C 29/151* (2013.01); *C10G 2/30* (2013.01); *C10J 3/20* (2013.01);
  (Continued)

(58) Field of Classification Search
  None
  See application file for complete search history.

(56) References Cited

U.S. PATENT DOCUMENTS 3,951,615 A   4/1976   Gernhardt et al.
3,966,633 A   6/1976   Friedman
(Continued)

FOREIGN PATENT DOCUMENTS

AU           777391        4/2001
CN         1769397 A       5/2006
(Continued)

OTHER PUBLICATIONS

Machine translation for WO 03-033624 A1. Retrieved from Espacenet website on Nov. 7, 2019. (Year: 2019).*

(Continued)

*Primary Examiner* — Jennifer A Leung
(74) *Attorney, Agent, or Firm* — Ostrolenk Faber LLP

(57) ABSTRACT

A process for the generation of energy and/or hydrocarbons and other products utilizing carbonaceous materials. In a first process stage (P1) the carbonaceous materials are supplied and are pyrolysed, wherein pyrolysis coke (M21) and pyrolysis gas (M22) are formed. In a second process stage (P2), the pyrolysis coke (M21) from the first process stage (P1) is gasified, wherein synthesis gas (M24) is formed, and slag and other residues (M91, M92, M93, M94) are removed. In a third process stage (P3), the synthesis gas (M24) from the second process stage (P2) is converted into hydrocarbons and/or other solid, liquid, and/or gaseous products (M60), which are discharged. The three process stages (P1, P2, P3) form a closed cycle. Surplus gas (M25) from the third process stage (P3) is passed as recycle gas into the first process stage (P1), and/or the second process stage (P2), and pyrolysis gas (M22) from the first process stage
(Continued)

(P1) is passed into the second process stage (P2), and/or the third process stage (P3).

27 Claims, 17 Drawing Sheets

(30) Foreign Application Priority Data

Jan. 22, 2010 (EP) .................................... 10151481
Feb. 23, 2010 (EP) .................................... 10154449

(51) Int. Cl.
| | | |
|---|---|---|
| *C10J 3/58* | (2006.01) | |
| *C10J 3/66* | (2006.01) | |
| *C10G 2/00* | (2006.01) | |
| *C07C 29/151* | (2006.01) | |
| *F01K 13/00* | (2006.01) | |
| *F02C 3/28* | (2006.01) | |

(52) U.S. Cl.
CPC . *C10J 3/40* (2013.01); *C10J 3/58* (2013.01); *F01K 13/00* (2013.01); *F02C 3/28* (2013.01); *C10G 2300/1011* (2013.01); *C10G 2300/1022* (2013.01); *C10G 2300/4037* (2013.01); *C10G 2300/4081* (2013.01); *C10J 2300/094* (2013.01); *C10J 2300/0959* (2013.01); *C10J 2300/0966* (2013.01); *C10J 2300/0969* (2013.01); *C10J 2300/1606* (2013.01); *C10J 2300/1659* (2013.01); *C10J 2300/1665* (2013.01); *C10J 2300/1671* (2013.01); *C10J 2300/1675* (2013.01); *C10J 2300/1693* (2013.01); *C10J 2300/1807* (2013.01); *C10J 2300/1823* (2013.01); *C10J 2300/1846* (2013.01); *C10J 2300/1884* (2013.01); *C10J 2300/1892* (2013.01); *F23C 2900/9901* (2013.01); *Y02E 20/12* (2013.01); *Y02E 20/326* (2013.01); *Y02E 50/12* (2013.01); *Y02P 30/20* (2015.11)

(56) References Cited

U.S. PATENT DOCUMENTS

| | | | |
|---|---|---|---|
| 4,076,612 A | 2/1978 | Hollaway | |
| 4,092,825 A | 6/1978 | Egan | |
| 4,660,465 A | 4/1987 | Jentzsch et al. | |
| 4,946,477 A | 8/1990 | Perka et al. | |
| 5,034,021 A | 7/1991 | Richardson | |
| 5,170,725 A | 12/1992 | Sass | |
| 5,265,410 A | 11/1993 | Hisatome | |
| 5,290,327 A * | 3/1994 | Rossle | C10J 3/66 110/222 |
| 5,849,050 A | 12/1998 | Wolf | |
| 6,170,264 B1 | 1/2001 | Viteri | |
| 6,178,899 B1 | 1/2001 | Kaneko | |
| 6,210,822 B1 | 4/2001 | Abersfelder et al. | |
| 6,455,011 B1 | 9/2002 | Fujimura et al. | |
| 10,450,520 B2 * | 10/2019 | Rudlinger | C10J 3/66 |
| 2001/0039760 A1 | 11/2001 | Cheng | |
| 2003/0083390 A1 | 5/2003 | Shah et al. | |
| 2003/0097840 A1 | 5/2003 | Hsu | |
| 2005/0247553 A1 | 11/2005 | Ichikawa | |
| 2005/0250862 A1 | 11/2005 | Bayle et al. | |
| 2006/0115691 A1 | 6/2006 | Hilmen et al. | |
| 2007/0129449 A1 * | 6/2007 | Topf | C10J 3/06 518/705 |
| 2007/0131909 A1 | 6/2007 | Rojey | |
| 2007/0163176 A1 | 7/2007 | Ruger et al. | |
| 2008/0040975 A1 | 2/2008 | Calderon | |
| 2008/0280338 A1 | 11/2008 | Hall | |
| 2009/0020052 A1 | 1/2009 | Becchetti et al. | |
| 2009/0145843 A1 | 6/2009 | Ahner | |
| 2009/0297993 A1 | 12/2009 | Fan et al. | |
| 2010/0257868 A1 * | 10/2010 | Craze | C10J 3/00 60/780 |

FOREIGN PATENT DOCUMENTS

| | | |
|---|---|---|
| CN | 1912070 A | 2/2007 |
| DE | 2325204 A1 | 12/1974 |
| DE | 2807326 | 8/1979 |
| DE | 19734911 A1 | 4/1998 |
| DE | 19807988 A1 | 9/1999 |
| DE | 10 2007 041624 A1 | 3/2009 |
| EP | 0520086 A2 | 12/1992 |
| EP | 0563777 A2 | 10/1993 |
| EP | 1167860 A2 | 1/2002 |
| EP | 1 526 165 A1 | 4/2005 |
| EP | 1749872 A2 | 2/2007 |
| JP | 06-346065 | 12/1994 |
| JP | 10-067992 | 3/1998 |
| JP | 2000-328071 | 11/2000 |
| JP | 2008-208297 | 9/2008 |
| WO | WO 00/70262 | 11/2000 |
| WO | WO 02/48292 | 6/2002 |
| WO | WO 03/033624 A1 | 4/2003 |
| WO | WO 2007/079381 A2 | 7/2007 |
| WO | WO 2008/011213 | 1/2008 |

OTHER PUBLICATIONS

International Search Report dated Mar. 7, 2011 issued in corresponding PCT International Patent Application No. PCT/EP2010/067847.

Hoffman B., "Verfahren zur Herstellung des synthetischen Biokraftstoffs SunDiesel Process for the production of the synthetic biofuel SunDiesel," Aufbereitungs Technik, Verlag Fuer Aufbereitung, Wiesbaden, DE, Bd. 49, Nr. ½, Jan. 1, 2008, Seiten 6-17, XP001510470, ISSN: 0004-783X in der Anmeldung erwähnt Abbildungen 3-6 Seiten 11-16.

Zwart R W R et al.: "High efficiency co-production of substitute natural as (SNG) and Fischer-Tropsch (FT) transportation fuels from biomass", Energy and Fuels Mar./Apr. 2005 American Chemical Society US LNKD-DOI:10.1021/EF049837W Bd. 19, Nr. 2, März 2005, Seiten 591-597, XP002578278, in der Anmeldung erwähnt Abbildungen 1,4.

Anders Evald (Force Technology, Denmark) and Janet Witt (Institute for Energy and Environment, Germany), "Biomass CHP best practice guide," Mar. 2006.

R.W. Zwart, H. Boerrigter, "High Efficiency Co-production of Synthetic Natural Gas (SNG) and Fischer-Tropsch (FT) Transportation Fuels from Biomass," Energy & Fuels 2005, 19, pp. 591-597. Contributions ECN Biomass to "The 2$^{nd}$ World Conference and Technology Exhibition on Biomass for Energy, Industry and Climate Protection", Conference Paper, Jul. 2004, ECN-RX.

George W. Huber et al.: "Synthesis of Transportation Fuels from Biomass: Chemistry, Catalysts, and Engineering", Chem. Rev. 2006, 106, pp. 4044-4098.

"Entrained Flow Gasifiers," http://www.ScienceDirect.com.

"Fluidized Beds," http://www.ScienceDirect.com.

H. Boerrigter et al., "Green Diesel From Biomass by Fischer-Tropsch Synthesis: New Insights in Gas Cleaning and Process Design," Presented at the PGBW Expert Meeting, Strasbourg, France, Oct. 1, 2002, pp. 1-15.

H. Boerrigter et al., "Liquid Fuels From Solid Biomass," Presented at the Biomass Gasification Conference, Leipzig, Germany, Oct. 1, 2003, pp. 1-18.

H. Boerrigter et al., "High Efficiency Co-Production of Fischer-Tropsch (FT) Transportation Fuels and Substitive Natural Gas (SNG) from Biomass," Feb. 2004, pp. 1-65.

H. Boerrigter et al., "Green Diesel from Biomass via Fischer-Tropsch Synthesis: New Insights in Gas Cleaning and Process

(56) References Cited

OTHER PUBLICATIONS

Design," Presented at Pyrolsis and Gasification of Biomass and Waste, Strasbourg, France, Oct. 1, 2002, pp. 1-13.

* cited by examiner (a)

THERMAL AND CHEMICAL UTILIZATION OF CARBONACEOUS MATERIALS, IN PARTICULAR FOR EMISSION-FREE GENERATION OF ENERGY

CROSS-REFERENCE TO RELATED APPLICATIONS

The present application is a divisional under 37 C.F.R. § 1.53(b) of prior U.S. patent application Ser. No. 13/509, 883, filed Jun. 1, 2012, which is a 35 U.S.C. § 371 national phase conversion of PCT/EP2010/067847, filed Nov. 19, 2010, which claims priority to European Patent Application No. 09176684.0, filed Nov. 20, 2009, European Patent Application No. 10151481.8, filed Jan. 22, 2010, European Patent Application No. 10151473.5, filed Jan. 22, 2010, and European Patent Application No. 10154449.2, filed Feb. 23, 2010. The entire content of each of these applications is incorporated in full by reference herein. The PCT International Application was published in the German language.

TECHNICAL FIELD

The invention relates to processes and facilities for emission-free generation of energy by thermal-chemical processing and utilization of solid, liquid and gaseous carbonaceous materials and mixtures, in particular of waste, biomass, coal and other heterogeneous materials. Further the invention relates to facilities for the generation of electrical and mechanical energy, and corresponding processes, as well as the manufacture of synthetic hydrocarbons and their use in such facilities.

PRIOR ART

It has been known for some time that emissions, particularly carbon dioxide emissions, have very adverse effects on the climatic equilibrium of earth, and contribute greatly to manmade climatic heating. Avoiding carbon dioxide emissions is therefore highly desirable, in particular in the generation of energy from carbonaceous materials, such as waste, biomass, and fossil fuels.

When carbonaceous materials are used as fuels in conventional power plant installations, carbon dioxide is an unavoidable by-product of energy generation. Separating out carbon dioxide from resultant combustion exhaust gases is generally not possible with a reasonable energetic and/or economic expenditure.

For the industrial scale, systems are being tested in which the carbon dioxide is trapped, for example, in amine-based solvents, and is stored in compressed form. However, such systems are expensive and complicated.

Energy sources without carbon dioxide emissions such as, for example, solar power, wind power, water power, and nuclear energy have other problems. Recent installations for using alternative energy sources such as wind power, solar energy and biomass have insufficient capacities for covering the steadily increasing energy demands. In addition, weather-dependent energy sources frequently cannot ensure unconditionally the necessary output capacities. Installations for low-emission, efficient, flexible and easily upscalable energy generation, in particular of electrical energy, are therefore a subject of intensive research activity.

From the prior art, various types of processes and installations are known with which gas mixtures can be produced from solid, liquid and gaseous carbonaceous materials, which are then used as so called synthesis gas for chemical syntheses. Synthesis gases containing carbon monoxide and hydrogen are used, for example, for industrial liquid-phase methanol synthesis or for Fischer-Tropsch synthesis for producing hydrocarbons and other organic materials. Alternatively, such synthesis gases are also used for generating energy, for example as a fuel for operating heat engines.

For producing carbon monoxide-hydrogen synthesis gases from solid carbon, the solid carbon is gasified using oxygen, carbon dioxide or water to form synthesis gas:

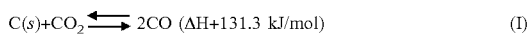 (I)

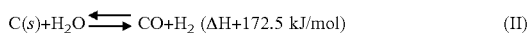 (II)

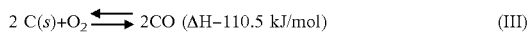 (III)

The ratio between carbon monoxide and hydrogen is given by what is termed the water gas shift reaction IV:

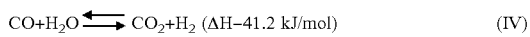 (IV)

The thermal energy required for the course of the endothermic reactions I and II can originate, for example, from a partial combustion of the solid carbon in reaction III, or can be supplied externally.

In a known process type for producing synthesis gas or corresponding gaseous fuel, the solid carbon for the gasification reactions is present in the form of coke. This is in turn generated in a preceding process stage by pyrolysis of coal or other carbonaceous materials. The pyrolysis gases formed during the pyrolysis are burned, wherein the hot carbon-dioxide-containing combustion gases serve firstly as gasification agent for the coke and also as an external heat energy supplier.

In another process type the coke is gasified with the addition of air/oxygen, wherein the thermal energy is primarily generated by partial combustion of the carbon of the coke. Pyrolysis gas from a preceding pyrolysis stage is then mixed into the hot synthesis gas where it is cracked, and so a tar-free combustible gas mixture is formed.

The known processes for producing synthesis gas are directed and optimized towards producing synthesis gas for the chemical industry from inexpensive fossil coal, for example for producing liquid propellant and other high-value end products. In these processes some of the starting material is burned for energy generation, and so in the production of high-value end products large amounts of no longer utilizable carbon dioxide are produced. Owing to manmade climatic warming, such inefficient processes are now becoming less and less acceptable.

Other processes are primarily directed towards producing more easily manageable gaseous fuel, from solid carbonaceous materials such as, for example, fossil coal, biomass, or heterogeneous mixtures such as, for example, combustible waste. With this fuel, for example, gas turbines can be run. Such processes are disclosed, for example, in DE 102007041624 A1 and DE 2325204 A1. However, also in these processes some of the chemical energy stored in the solid starting material is consumed in the conversion, either in the production of coke or the production of gas, and carbon dioxide is correspondingly discharged.

A disadvantage of the known processes is the generation of emissions, the low efficiency, and the complicated structure and operation, particularly in installations in which coke is gasified in a fluidized stream or entrained flow.

Likewise, various processes are known with which liquid propellants can be produced from biomass. In the article by G. W. Huber et al., "*Synthesis of Transportation Fuels from Biomass: Chemistry, Catalysts, and Engineering*", Chem. Rev. 106 (2006), p. 4044, a review of the various approaches is given. In a certain basic type of these processes, biomass is gasified and from the resultant gas mixture then gaseous and/or liquid hydrocarbons and/or other carbonaceous compounds are synthesized that serve as propellant or fuel.

Such a process for producing synthetic propellant from biomass is described in "*Process for Producing the Synthetic Biofuel SunDiesel*" [English translation of German title "*Verfahren zur Herstellung des synthetischen Biokraftstoffs SunDiesel*"], B. Hoffmann, Aufbereitungstechnik, 49(1-2) (2008), p. 6. In this process, which is called "Carbo-V", lumpy biomass (comminuted plant material) is pyrolysed with air in a first step at low pressure (4 bar) at 400-500° C., wherein this step is considered as a thermal pretreatment step. This produces pyrolysis gas and pyrolysis coke. A corresponding installation is disclosed for example in DE 19807988 A1. The pyrolysis gas is then post-oxidized with preheated air or oxygen at high temperature (1400-1500° C.) in order to break down long-chain hydrocarbons. Separately therefrom, the pyrolysis coke is ground and blown in dust form into the gas stream of the second process stage where the coke dust is endothermically gasified to synthesis gas in entrained flow. A corresponding process is disclosed in EP 1749872 A2. After a treatment, propellant analogous to diesel is produced from the resultant synthesis gas, in a multistage Fischer-Tropsch synthesis. Resultant exhaust gases including the carbon dioxide produced in the pyrolysis and gasification stage are released into the atmosphere.

In order to increase the efficiency of the Fischer-Tropsch reaction, the residual gases and gaseous products of the Fischer-Tropsch synthesis which contain unreacted hydrogen and carbon monoxide and also C1-C4 hydrocarbon compounds, can again be passed through the Fischer-Tropsch stage by recirculating them to the gasification stage. (cf. H. Boerrigter, R. Zwart, "*High efficiency co-production of Fischer-Tropsch (FT) transportation fuels and substitute natural gas (SNG) from biomass*", Energy research centre of the Netherlands ECN Report, ECN-C-04-001, February 2004). Thus, for example US 2005/0250862 A1 shows a process for producing liquid propellants from biomass in which low-molecular-weight gases and unwanted higher-molecular-weight fractions are passed back to the gasification stage, downstream of the Fischer-Tropsch synthesis.

However, in all these processes, exhaust gases consisting principally of carbon dioxide and also if applicable inert gases such as atmospheric nitrogen are released to the atmosphere.

DE 2807326 and U.S. Pat. No. 4092825 describe power plant installations in which synthesis gas is produced from coal, which synthesis gas is then used as fuel gas for steam generation. Via a steam turbine, electrical energy is produced from the steam. Some of the synthesis gas is branched off and used for producing methanol or liquid hydrocarbons. These liquid fuels are stored temporarily and used as required for generating electrical energy. The resultant combustion exhaust gases are released into the atmosphere.

The disclosure of the prior art documents cited in this application forms an integral component of the following description of the invention.

OBJECT OF THE INVENTION

It is the object of the invention to provide processes and facilities for the emission-free generation of energy by thermal-chemical processing and utilization of solid, liquid and gaseous carbonaceous materials and mixtures, in particular of waste, biomass, coal and other heterogeneous materials, which processes and installations do not have the above-mentioned and other disadvantages. Particularly processes and facilities according to the invention should be as emission-free as possible.

Another object of the invention is to provide processes and facilities by means of which waste, biomass or coal can be converted with as little energy supply as possible, and emission-free, into other energy-rich products, for example synthetic hydrocarbon containing products.

One more object of the invention is to provide processes and facilities by means of which materials that are difficult to utilize, such as for example oil shale, oil sand or oil sludge, can be converted in an emission-free manner into energy-richer and more useful products, or can be used for emission-free energy generation, respectively.

A further object of the invention is to provide processes and facilities with which solid, liquid or gaseous materials can be efficiently converted into gaseous or liquid energy sources.

Another object of the invention is to provide processes and installations by means of which solid, liquid and gaseous fuels and propellants can be generated emission-free.

Yet another object of the invention is to optimize the energy efficiency of said processes and facilities, by avoiding chemical and/or energetic losses due to emissions, and by converting the collected non-emitted materials into additional high-grade energy sources, such as for example fuels and propellants.

A facility for energy generation according to the invention should, in particular, allow the provision of electrical energy and/or mechanical energy and/or thermal energy, efficiently and according to demand in a broad output band.

Advantageously, such a facility according to the invention for emission-free energy generation should be able to store part of the generated energy, and in the event of increased output demand should be able to release again this stored energy as chemical energy and/or electrical energy and/or mechanical energy and/or thermal energy.

A facility for emission-free energy generation should advantageously be able to utilize a broad range of solid, liquid and/or gaseous carbonaceous materials and mixtures for energy generation, in particular waste, biomass, coal and other heterogeneous materials.

A further object of the invention is to provide a facility for emission-free energy generation that is independent of external conditions such as pressure, temperature, moisture or other external parameters. For example, at relatively elevated locations, the lower ambient pressure has adverse effects on the output power of conventional power installations.

These and other objects are achieved by processes and facilities according to the invention as described in the independent claims. Further advantageous embodiments are given in the dependent claims.

DESCRIPTION OF THE INVENTION

In a process according to the invention for the emission-free generation of energy and/or hydrocarbons and other products by utilization of carbonaceous materials, in a first process stage the carbonaceous materials are supplied and pyrolysed, wherein pyrolysis coke and pyrolysis gas are formed. In a second process stage, the pyrolysis coke from the first process stage is gasified, wherein synthesis gas is formed, and slag and other residues are removed. In a third process stage, the synthesis gas from the second process stage is converted into hydrocarbons and/or other solid, liquid and/or gaseous products, which are discharged. The three process stages form a closed cycle. Surplus gas from the third process stage is passed as recycle gas into the first process stage and/or the second process stage, and the pyrolysis gas of the first process stage is passed into the second process stage and/or the third process stage.

In an advantageous variant of this process, hydrogen is supplied, preferably in the third process stage, and/or carbon dioxide is supplied, preferably in the first process stage or the second process stage.

The process can be carried out under pressure in all three process stages. The pyrolysis gas from the first process stage can be passed into the second process stage and/or into the third process stage. The synthesis gas from the second process stage can in turn be passed into the third process stage and/or the first process stage.

Advantageously, the gas stream within the cycle proceeds in a defined direction. The gas stream can for example flow within the cycle from the first process stage via the second process stage to the third process stage, and back to the first process stage, or from the first process stage via the third process stage to the second process stage, and back again to the first process stage.

Particularly advantageously, there is a pressure drop along the cycle. This allows the gas stream to be conveyed along the cycle without an additional transport system, with the exception of a compressor for generating the pressure drop.

The first process stage of the utilization process can be carried out in one or more pressure reactors.

The heat energy for the pyrolysis reactions in the first process stage can be provided in part or completely by returning a part of the hot synthesis gas from the second process stage into the first process stage, and/or by partial oxidation of the carbonaceous starting material and the resultant pyrolysis coke.

Advantageously, the first process stage is carried out at a temperature between 300 and 800° C., preferably between 450 and 700° C., and particularly preferably between 500 and 600° C.

The second stage of the utilization process can likewise be carried out in one or more second pressure reactors. For the gasification reaction in the second process stage, oxygen and/or steam and/or carbon dioxide can be used as gasification agent.

The pyrolysis coke can be gasified completely or only in part. In the latter case, the unprocessed coke can be discharged together with the resultant slag.

The thermal energy required for the gasification reaction in the second process stage can be supplied in part or completely from outside, for example by heating devices and/or heat exchangers, and/or can be generated by oxidizing a part of the pyrolysis coke with an oxidizing agent, in particular oxygen.

Advantageously, the second process stage of the utilization process according to the invention is carried out at a temperature between 600 and 1600° C., preferably between 700 and 1400° C., and particularly preferably between 850 and 1000° C.

In a preferred variant the temperature in the second process stage is 850° C. or above, wherein the pyrolysis coke and the pyrolysis gases remain in the second process stage for at least 2 seconds. In this manner, the provisions are met that apply in many countries for treating contaminated materials and wastes.

Advantageously, the first process stage and/or the second process stage of the utilization process according to the invention is carried out at a pressure between 1 and 60 bar, preferably between 5 and 25 bar, and particularly preferably between 10 and 15 bar.

In another advantageous variant of the utilization process according to the invention, the first process stage and the second process stage are carried out in the same pressure reactor.

The third process stage of the utilization process is advantageously carried out in one or more pressure reactors. The conversion in the third process stage preferably proceeds using a Fischer-Tropsch synthesis or a liquid-phase methanol synthesis.

In a particularly advantageous variant of the process according to the invention, electrical and/or mechanical energy is generated by oxidation of the hydrocarbons and other solid, liquid, and/or gaseous products of the third process stage, to an oxidation gas essentially consisting of carbon dioxide and water. Advantageously pure oxygen is used as oxidizing agent. From the oxidation gases, water can be condensed out and/or separated.

In an advantageous variant of such a process according to the invention, at least a part of the oxidation gases of the drive device is re-fed back into the first process stage and/or the second process stage and/or the third process stage of the process.

In a particularly advantageous variant of a process according to the invention, synthesis gas is cooled in a heat exchanger, wherein superheated steam and/or another hot gas are formed, from which electrical and/or mechanical energy is generated using a heat engine, preferably a steam turbine.

A facility according to the invention for the emission-free generation of energy and/or hydrocarbons and other products by utilization of carbonaceous materials comprises a utilization installation containing a utilization unit with a first subunit for carrying out a pyrolysis of the carbonaceous materials to form pyrolysis coke and pyrolysis gas; a second subunit for carrying out a gasification of the pyrolysis coke to form synthesis gas and residues; and a third subunit for carrying out a conversion of the synthesis gas into hydrocarbons and/or other solid, liquid and/or gaseous products. All three subunits of the utilization unit are pressure-tightly closed and form an essentially closed cycle. A transport pipe for the pyrolysis gas connects the first subunit pressure-tightly to the second subunit and/or to the third subunit. A transport pipe for the synthesis gas connects the second subunit pressure-tightly to the third subunit and/or to the first subunit. A transport pipe for the recycle gas connects the third subunit pressure-tightly to the first subunit and/or to the second subunit.

Advantageously, at least one compressor is arranged along at least one of said transport pipes.

Means can be provided that cause a gas stream to flow along the transport pipes in only one defined direction, preferably from the first subunit via the second subunit to the third subunit, and back to the first subunit, or from the first subunit via the third subunit to the second subunit, and back to the first subunit.

The subunits can each have one or more pressure reactors. In an advantageous variant, the first and/or the second subunit comprise heating devices and/or heat exchangers.

A branching of the transport pipe of the synthesis gas can be provided, by means of which some of the synthesis gas, from the second subunit can be returned to the first pressure reactor.

In another advantageous variant of a facility according to the invention, the first subunit and the second subunit of the utilization unit comprise a shared pressure reactor.

The third subunit of the utilization unit preferably comprises a Fischer-Tropsch synthesis installation, or a liquid-phase methanol synthesis installation, or another suitable installation for producing liquid products.

Particularly advantageous is a utilization installation that can be run in such a manner that there is a pressure drop from the first process stage over the second process stage to the third process stage. In this way, the mass transport along the cyclic gas stream is driven by the pressure difference between the various pressure reactors. This is a substantial advantage, since this leads to the installation requiring as few moving components as possible.

A particular advantage of the invention is that the facility is independent of external conditions such as pressure, temperature, moisture, or all other external parameters. Since in facilities according to the invention the matter stream proceeds in a closed manner, the process is substantially independent of the ambient pressure.

A further substantial advantage of a facility according to the invention is that the closed system does not require a gas treatment. It is a further advantage that the formation and separation of liquid products from the synthesis gases in the third process stage inevitably leads to particles being separated out.

A particularly advantageous embodiment of a facility according to the invention comprises an energy installation that is arranged for generating electrical and/or mechanical energy and/or thermal energy, using the hydrocarbons and/or other products from the utilization installation as fuels. Advantageously, a drive device for generating electrical and/or mechanical energy from the fuels is provided in the energy installation, wherein said drive device obtains the energy necessary for operation from the oxidation of the fuels to an oxidation gas essentially consisting of carbon dioxide and water, and comprises a device for the compression and/or condensation of the oxidation gas.

The drive device can be designed as a fuel cell or as a heat engine. In a particularly advantageous variant, the drive device can be operated with pure oxygen as oxidizing agent.

In a further embodiment of a facility according to the invention, a heat exchanger is provided for cooling down the oxidation gas stream, upstream and/or downstream of the device for the compression and/or condensation of the oxidation gas.

In yet a further embodiment of a facility according to the invention, a device for condensation and/or separation of water from the oxidation gas is provided. This reduces, inter alia, the amount of the remaining residual gas.

Another variant of such a facility according to the invention comprises a storage for collecting the oxidation gas, or the residual gas after compression and/or condensation of the oxidation gas, respectively.

For recirculating the oxidation gases or residual gases into one of the three process stages of the utilization installation of a facility according to the invention, a transport pipe can be provided.

In another advantageous embodiment of one of the above-mentioned facilities according to the invention, the drive device of the energy installation is designed as a combustion engine, with at least one combustion chamber for combustion of liquid or gaseous fuel with oxygen, with means for converting the resulting gas pressure or gas volume into mechanical work, with a feed device for introducing oxygen into the combustion chamber, and with a venting device for removing the oxidation gases from the combustion chamber.

In a particularly advantageous variant of such a facility for energy generation according to the invention, the drive device of the energy installation is provided with a feed device for introducing water and/or water vapor into the combustion chamber, and/or into the oxidation gas stream after exit from the combustion chamber. The drive device can comprise, for example, a turbine device that is operated with the oxidation gas stream.

In a further advantageous variant of a facility according to the invention, the utilization installation comprises an energy unit for generating electrical and/or mechanical energy, with at least one drive device for generating electrical and/or mechanical energy from steam and/or other hot gases that have been generated or superheated in the utilization unit of the utilization installation.

In a particularly advantageous variant, the energy unit of the utilization installation comprises a drive device for generating electrical and/or mechanical energy from steam or other hot gases that have been generated or superheated in the utilization unit. In the cycle of the utilization unit at least one heat exchanger is provided for heating steam and/or other gases, and/or for generating steam.

A further particularly advantageous facility comprises an installation for the production of hydrogen, and means for supplying the hydrogen into the utilization unit.

Hydrocarbons and other solid, liquid and/or gaseous products that have been produced using a process according to the invention, or using a facility according to the invention, respectively, can be differentiated from analogous petroleum products for example by the absence of typical sulphur and phosphorus impurities. In the case of a production with fractions of the starting material being biomass, such products have an elevated C14-isotope fraction, compared with petrochemical products.

BRIEF DESCRIPTION OF THE DRAWINGS

Hereinafter the facility according to the invention will be described with reference to drawings. These show only exemplary embodiments of the subject matter of the invention.

MODES OF CARRYING OUT THE INVENTION

The examples discussed hereinafter are provided for an improved illustration of the present invention, but are not suited for restricting the invention to the features disclosed herein.

Installation and Process for Generating Electrical and Mechanical Energy

Figure 1:
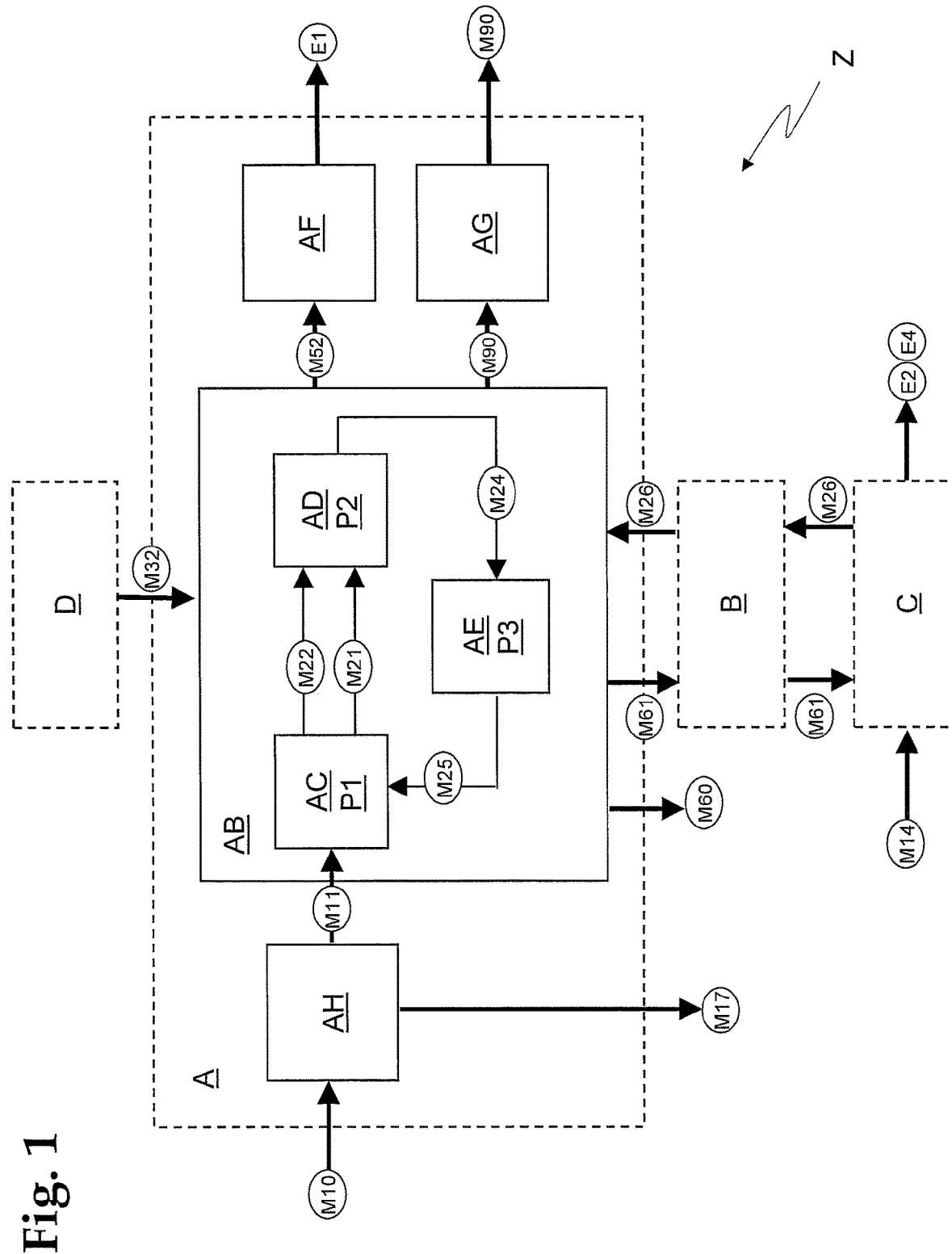
FIG. 1 schematically shows a facility according to the invention for emission-free generation of energy and/or hydrocarbons and other products by utilization of carbonaceous materials.

FIG. 1 schematically shows a possible embodiment of a facility Z according to the invention for the emission-free generation of energy and/or hydrocarbons and other products by utilization of carbonaceous materials, having a utilization installation A for the thermal-chemical utilization of carbonaceous materials M10 to give hydrocarbons and other products M60 and/or liquid and/or gaseous fuels M61 (chemical energy), as well as the generation of electrical and/or mechanical energy E1.

The utilization installation A comprises a feeding unit AH, in which the untreated carbonaceous starting material M10 that should be utilized is processed to carbonaceous starting material M11. Depending on the kind of starting material M10, residues M17 can incur, which may be further used, e.g. metals.

In addition to the treated carbonaceous starting material M11, other chemical energy sources can be utilized, e.g. methane or other by-products from the chemical industry or the petroleum industry that cannot be reasonably utilized otherwise.

The centerpiece of the utilization installation A is the utilization unit AB, in which in a first subunit AC of a first process stage P1 the treated carbonaceous materials M11 are supplied to and get pyrolysed, wherein pyrolysis coke M21 and pyrolysis gas M22 are formed. In a second subunit AD of a second process stage P2, the pyrolysis coke M21 from the first process stage is gasified, wherein synthesis gas M24 is formed, and slag and other residues M90 remain. In a third subunit AE of a third process stage P3, the synthesis gas M24 from the second process stage is converted into hydrocarbon-based solid, liquid, and/or gaseous products M60, M61. All three process stages are pressure-tightly closed, and form a substantially closed cycle.

Thermal energy occurring in the utilization process according to the invention can be gathered from the first utilization unit AB in the form of steam M52, and can be used in an energy unit AF for generating electrical and/or mechanical energy E1, by means of a suitable drive device, for example a steam turbine (not shown). Also possible and advantageous is the heating of compressible media, such as for example nitrogen, for operating the drive device. During constant operation of the utilization unit AB, in this manner a certain base output power can be generated. The energy unit AF is an optional component of a facility according to the invention.

A discharging unit AG is used for discharging and treating the accumulating ash and other solid residues M90.

The facility according to the invention can further comprise an energy installation C for the emission-free generation of electrical and/or mechanical energy E2, or thermal energy E4, by utilizing the carbonaceous products M61 from the utilization installation A as fuels. Resulting oxidation gases M27 are lead back to the utilization installation A, and so no emissions occur.

The energy installation C can be designed as a heating installation for the generation of thermal energy E4 for heating buildings. Alternatively the energy installation can be designed as an electrical power plant installation for the generation of electrical energy E2.

Between the utilization installation A and the energy installation C, advantageously an installation B for the transport and temporary storage of the fuels and oxidation gases is inserted. Such an installation B can also comprise means for treating the fuels M61 to be used in the energy installation C.

The hydrocarbon-containing fuels M61 generated in the synthesis process stage P3 are temporarily stored in tanks or pressure storages of the installation B (not shown). From these storages, the fuels M61 are gathered as required, and are converted in the energy installation C into electrical and/or mechanical energy E2, using a suitable drive device. This can take place for example by means of a heat engine or a fuel cell device. Carbon dioxide-containing residual gas M26 from the energy installation C is recirculated back to the utilization unit AB. If appropriate, a temporary storage can be provided.

The energy installation C offers the advantage that the energy output produced by the facility Z according to the invention can be adapted in a very short time to the currently required demand. The chemical fuels M61 act in this case as a temporary energy storage. During a power consumption peak, for example a suitably designed drive device, for example a gas turbine and/or steam turbine operated with the fuels M61, can then be very rapidly put in operation, and generate electrical and/or mechanical energy. The peak output of the facility Z can exceed the thermal base output of the facility Z for a short time, owing to the energy storage capacity of the chemical fuels M61.

It is possible to use in an energy installation C further additional fuels M14, in addition to the fuels delivered by the utilization installation A.

Figure 2:
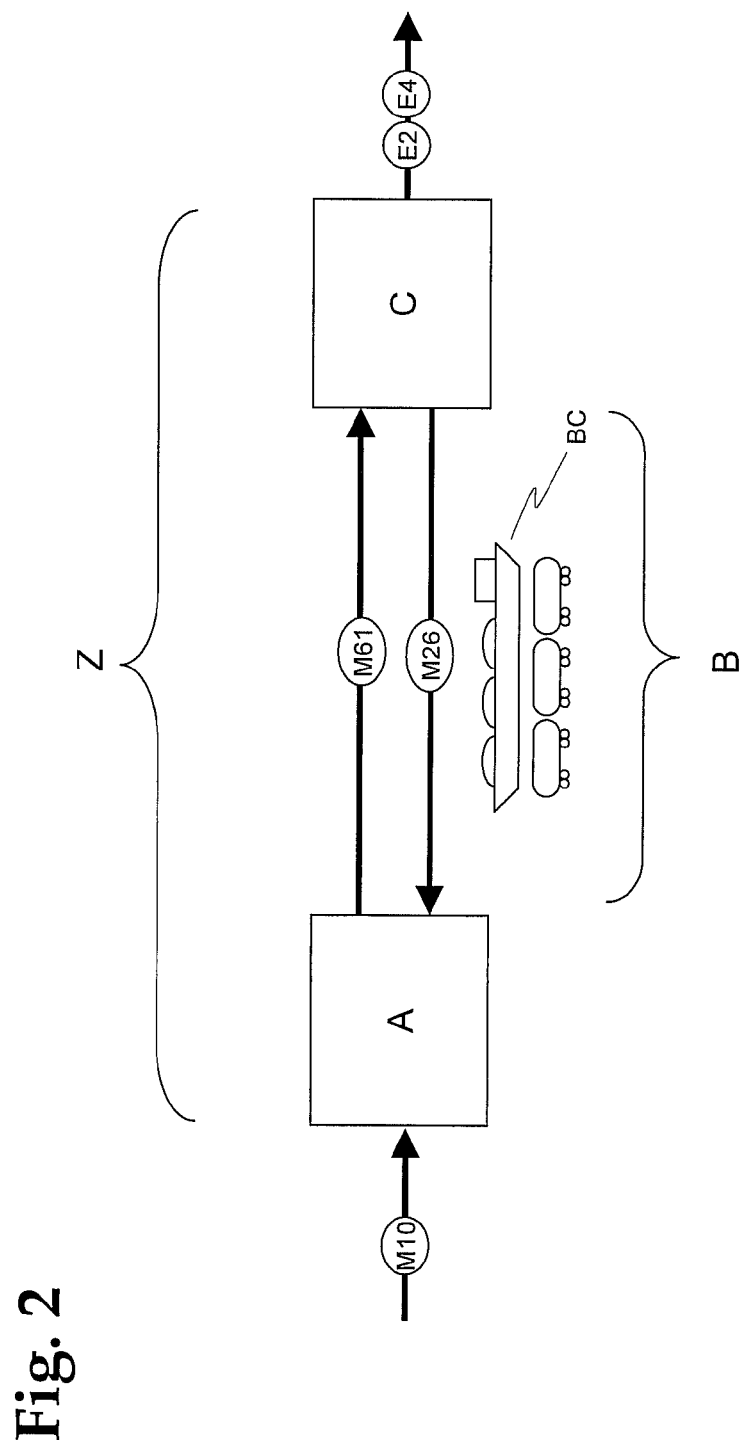
FIG. 2 schematically shows an embodiment of a facility according to the invention with an energy installation that is spatially separated from the utilization installation.

The energy installation C can be installed together with the utilization installation A at the same site. Alternatively, it is also possible, as shown in FIG. 2, that in a facility Z according to the invention the energy installation C is arranged spatially separated from the utilization installation A. The fuels M61 and the oxidation gases M27 can be transported for example by rail, ship, or pipeline, wherein in such a case the transport device (tank wagon, storage tank on ship, pipeline) at the same time acts also as temporary storage BA, BB. The overall system of material transport between installations A and C is in this case to be seen as a part of the installation B for transport and temporary storage of fuels and oxidation gases.

Since the transport of chemical energy in the form of fuels M61 over great distances is substantially more efficient than the transmission of electrical energy, the site of the peak load energy installation C of a facility Z according to the invention can be selected to be where the corresponding demand occurs, whereas the utilization installation A is advantageously constructed where the carbonaceous starting materials M10 occur.

Figure 6:
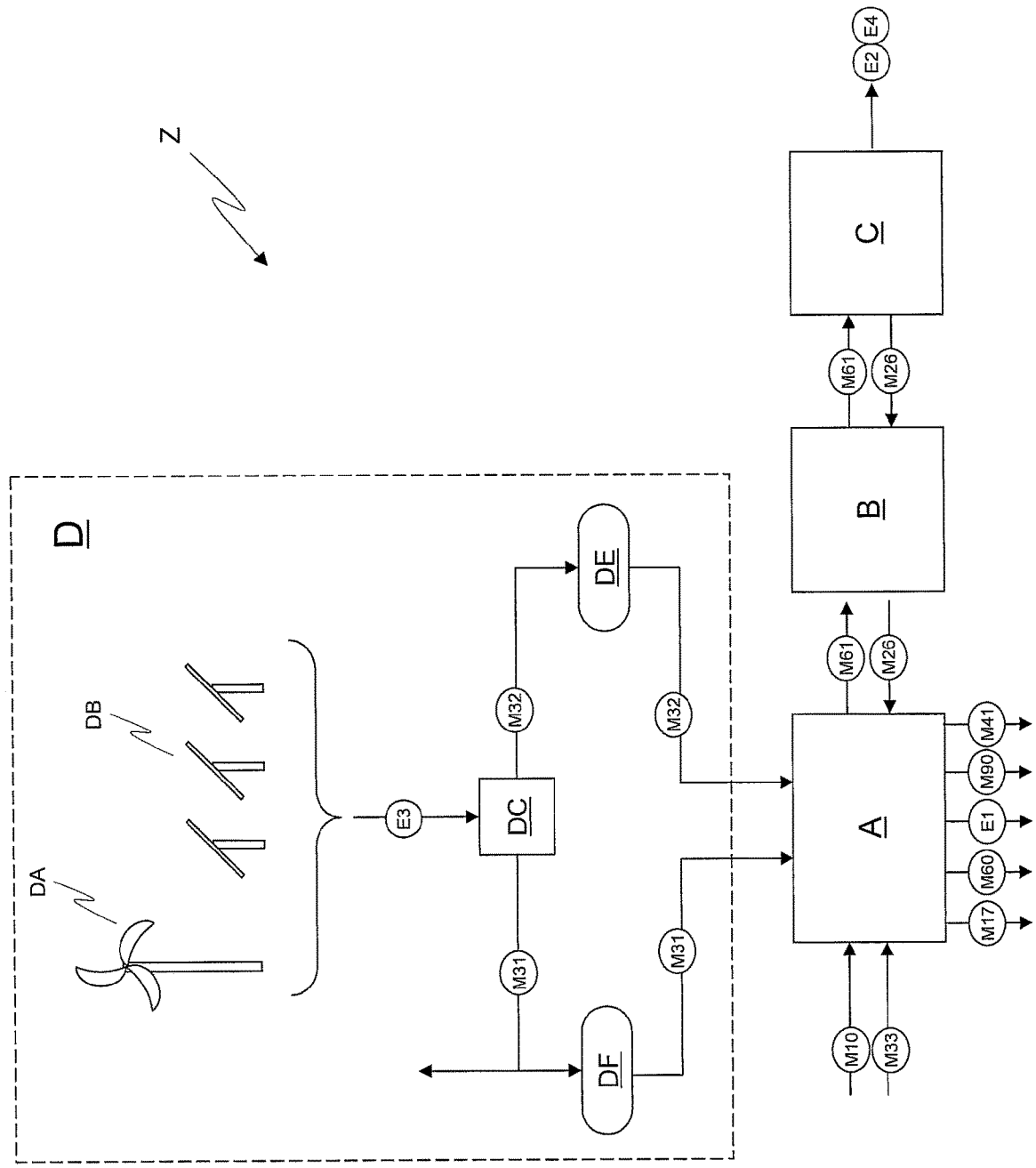
FIG. 6 schematically shows a facility according to the invention having supply of chemical energy in the form of hydrogen.
Figure 6:
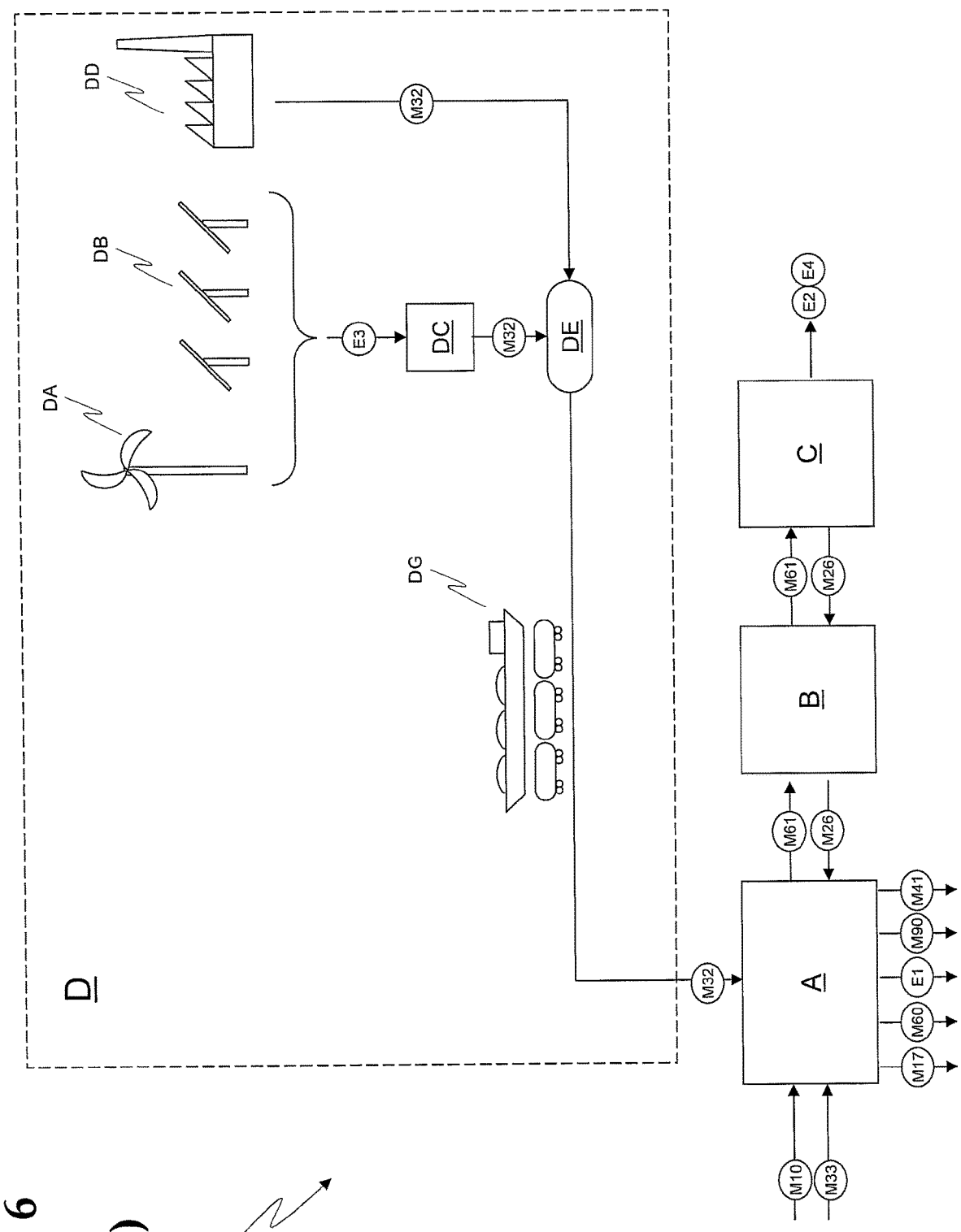

A facility according to the invention can further comprise an installation D for generation and supply of external chemical energy. For example, hydrogen M32 can be produced and supplied as source of external chemical energy. Such a possible embodiment of a facility Z according to the invention will be treated in more detail in the discussion of FIG. 6.

Figure 3:
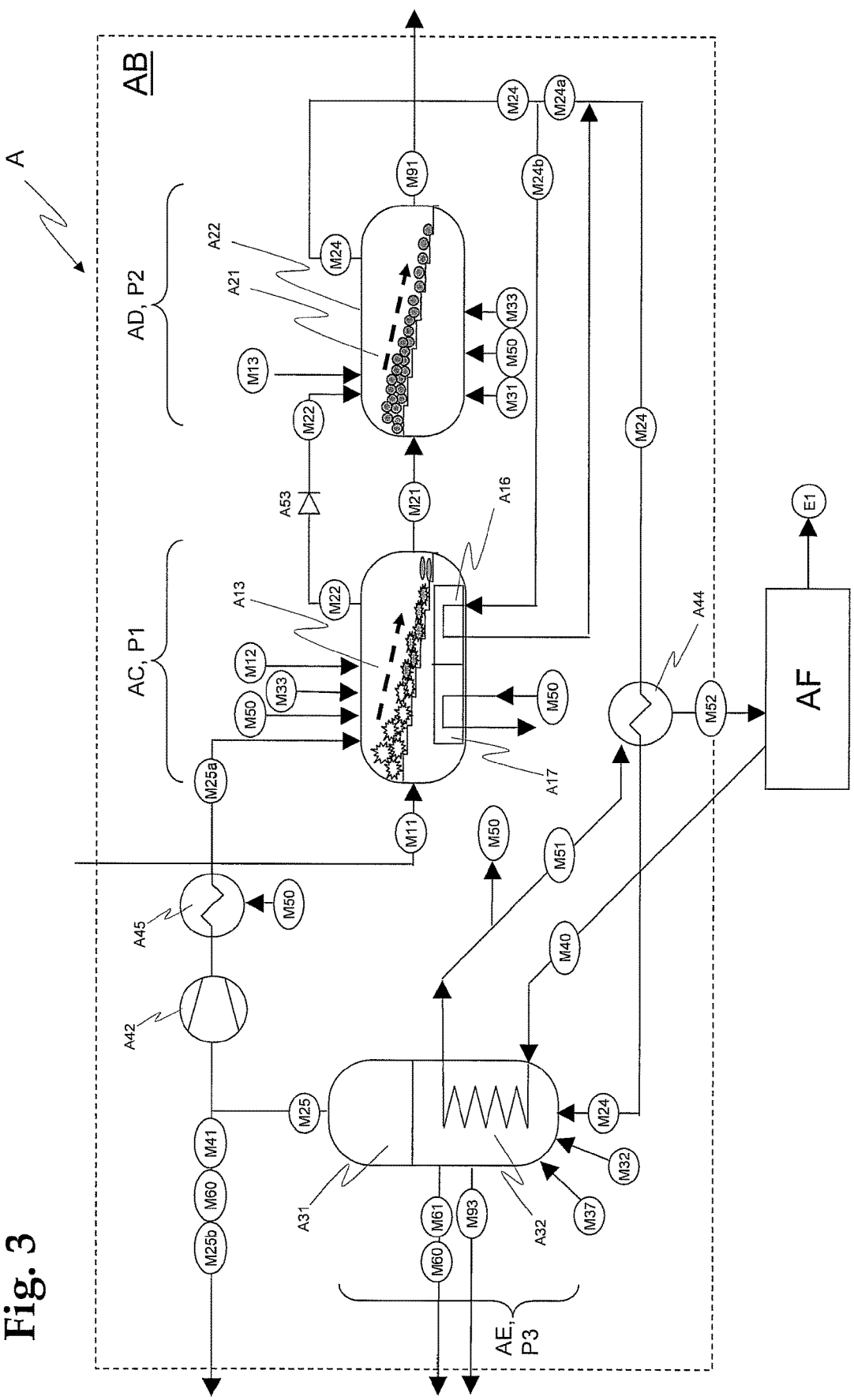
FIG. 3 schematically shows a general exemplary embodiment of a utilization installation of a facility according to the invention with a base load energy unit.

A possible embodiment of a utilization installation A of a facility Z according to the invention is schematically shown in FIG. 3. The shown installation A comprises a utilization unit AB for utilizing the carbonaceous starting material M11, and an energy unit AF for generating an essentially constant base amount E1 of electrical and/or mechanical energy.

The structure of the utilization unit AB corresponds essentially to the exemplary utilization unit that will be discussed later with reference to FIG. 9. The base load energy unit AF is only depicted as a block. A possible embodiment will be discussed in FIG. 3A.

In the heat exchanger/superheater A44, in which at the same time the hot synthesis gas M24 from the second process stage P2 is cooled down to the temperature for the third synthesis process stage P3, superheated steam M52 is generated (approximately 550-600° C./50 bar) from colder steam M51. If required, a subsequent further heat exchanger can further cool down the synthesis gas stream. The superheated steam M52 is lead into the energy unit AF, where it is utilized for generation of electrical and/or mechanical energy E1. The remaining steam condensate M41 is conducted back to the utilization unit AB, where it is converted in the third process stage P3 into steam M51, and this steam M51 is subsequently converted again in the heat exchanger/superheater A44 into superheated steam M52.

Figure 3A:
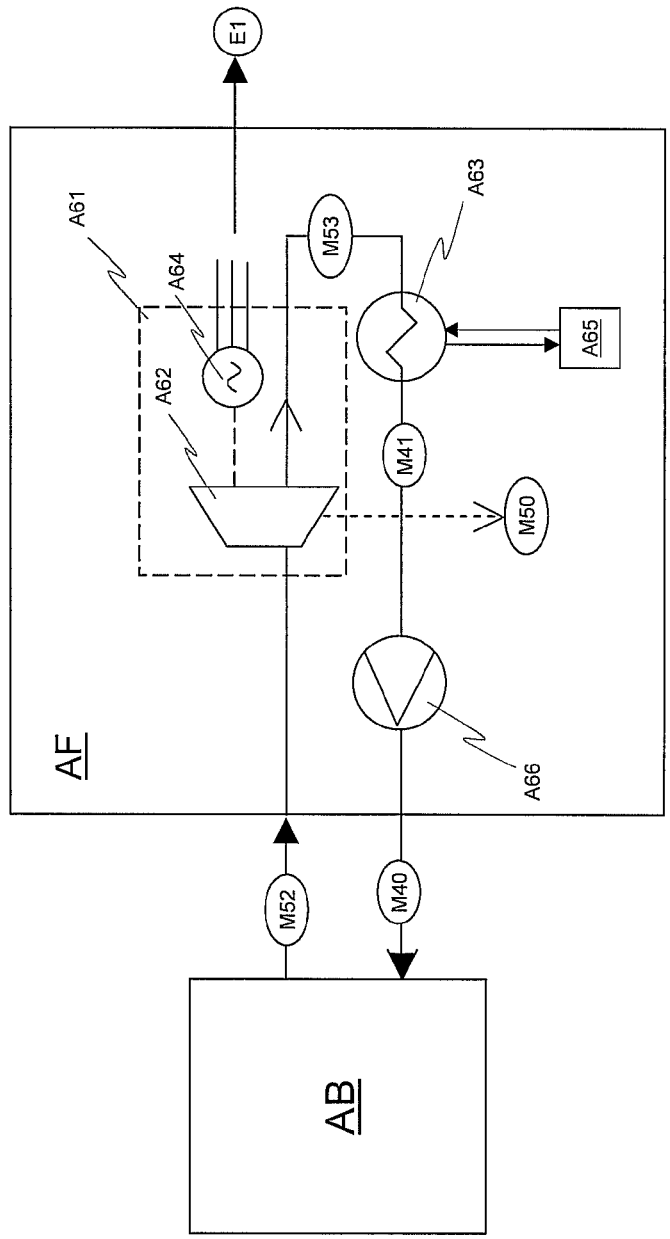
FIG. 3A schematically shows a possible variant for a base load energy unit as shown in FIG. 3.

The exemplary embodiment of the energy unit AF in FIG. 3A comprises a drive device A61 in the form of a steam turbine A62, or another heat engine for the generation of mechanical energy that can be operated with superheated steam M52, and in the given example a generator device A64, which generates electrical energy E1. After expansion in the steam turbine A62, the exhaust steam M53 is condensed in the condenser/economizer A63, wherein the waste heat is discharged via a suitably designed cooling cycle A65.

The resultant condensate M41 is preferably at a temperature of 60-70° C., and so the water in the subsequent boiler stage A32 of the utilization installation AB does not need to be heated too much. At the same time, the water should not be too hot, in order to prevent cavitation in the pump A66. The condensate M41 is transported by the pump A66 from a temporary storage (not shown) into the heat exchanger/boiler A32 of process stage P3, where it is in turn vaporized to steam M51 (approximately 250-300° C./20 bar), with simultaneous cooling of the synthesis stage P3. The steam M51 is stored in a vapor dome (which is not shown), in order firstly to separate off remaining water before entry into the superheater A44, and secondly to form a storage from which process steam M50 can obtained for the various purposes in the utilization unit AB. Losses in the cycle and consumption of process steam M50 are compensated for by new supply of water into the condensate storage (not shown).

In an alternative variant, in the steam turbine A62, downstream of the high-pressure stage, some of the steam can be extracted as process steam M50, which is shown in FIG. 3A as a dashed arrow. In this manner, a larger amount of steam M52 can be utilized for energy generation, and only thereafter the necessary process steam is provided.

The exhaust steam from process steam consumers such as for example the heat exchangers A45, A17 can likewise be condensed M41 and recirculated to the feed water M40, resulting in an energy cycle which that is closed as far as possible.

Instead of operating the energy unit AF with hot steam, it is also possible to heat in a compressible medium in the heat exchangers A32, A44 of the utilization unit, such as for example nitrogen, for subsequently using this hot gas for operating the heat engine of the energy unit AF. The use of inert gas instead of more aggressive hot steam has among other things the advantage that corrosion damages of the installation components are reduced.

Correspondingly, in a utilization installation A the steam cycles may also be conducted differently through the various heat exchangers, in order to achieve an efficiency of the installation A as high as possible.

In a facility according to the invention only having a base load energy unit AF, as is disclosed for example in FIG. 3, the products formed in the synthesis stage P3 can be used as fuel M61 for a conventional energy installation C that can be operated using fossil fuels, for example diesel generators or gas turbine generators, which can be used for covering peak loads. The chemical fuels M61 in such a case serve for achieving for a short time very high production outputs, independent from the base system AB, AF that is run in an equilibrium state. Thus, within a very short time period, the total output power of a facility Z according to the invention of for example 100% constant base load production $P_{c2}$ can be increased to for example 600% peak load production $P_{e2}$.

Alternatively, the products M60 can also be used in other ways, for example for producing fuels, or as reactants for the chemical industry.

Such a facility according to the invention has, compared with conventional installations, inter alia the advantage that owing to the closed material stream within the three-stage process, flue gas filters and catalyst devices for purifying the combustion exhaust gases can be dispensed with in the utilization unit AB. This leads to a reduction of the number of components of such an installation, and thereby to lower investment costs and operating costs.

In addition, such a utilization unit also has a lower space requirement, since no filter systems, stacks, etc. are required, and the volumes of the material streams are lower owing to the high pressure.

Figure 4:
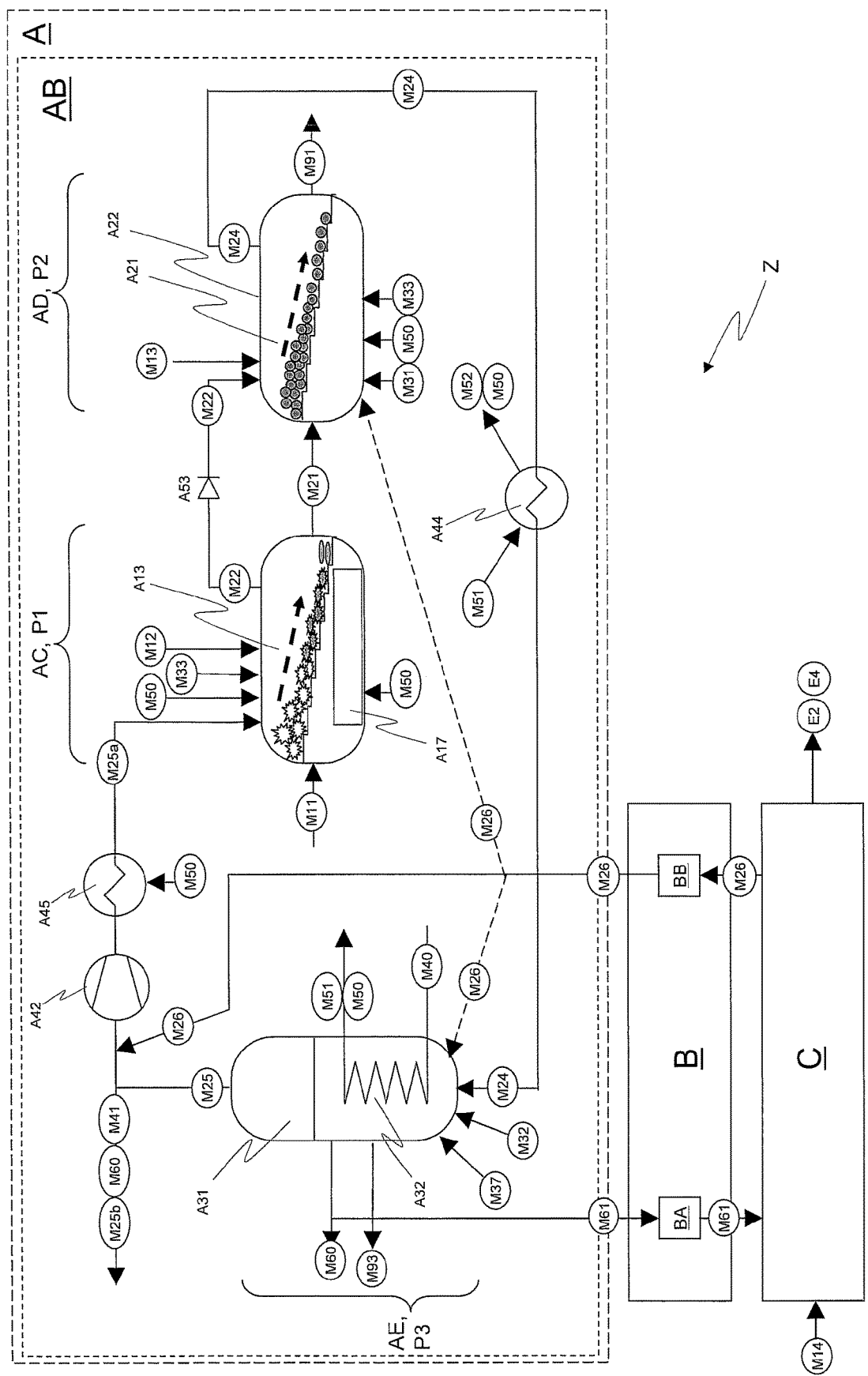
FIG. 4 schematically shows a general exemplary embodiment of a facility according to the invention, with a utilization installation, and an energy installation for the generation of peak load energy from the fuel compounds produced in the utilization installation.

In a particularly advantageous embodiment of a facility Z according to the invention, as is disclosed schematically in FIG. 4, an energy installation C for covering peak loads E2 is provided that can be operated with fuels M61 from the utilization installation A. The energy installation C is designed in such a manner that the carbon dioxide accumulating during energy generation is conducted back into the cycle of the utilization installation A, and so no emissions are formed.

The fuels M61 are advantageously obtained from a temporary storage BA of the transport/storage installation B, for example a tank system or pressure storage, in order to bridge demand peaks. The occurring carbon dioxide containing residual gases M26 from the energy installation B can also be collected and stored in a temporary storage BB.

Figure 4A:
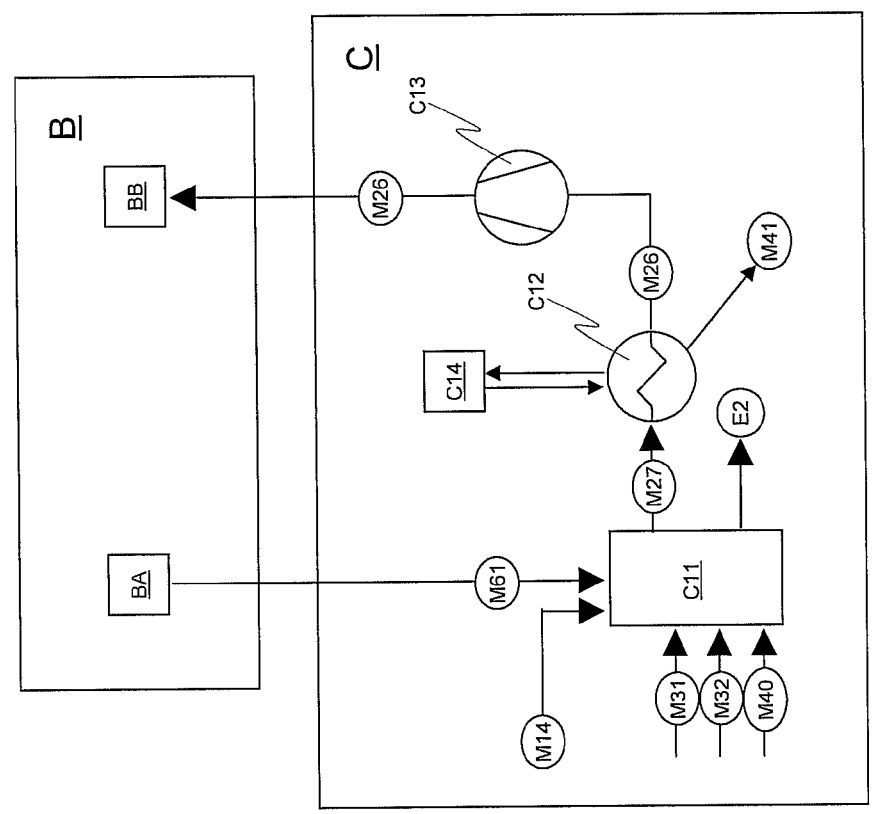
FIG. 4A schematically shows a possible variant for a peak load energy installation as shown in FIG. 4.

A possible embodiment of an energy installation C is shown in FIG. 4A. A drive device C11 generates electrical and/or mechanical energy E2 by means of chemical energy sources M61 from the synthesis stage P3 of the utilization unit AB. The said drive device C11 can be for example a heat engine, in which the heat occurring during an oxidation of the fuels M61 to carbon dioxide is converted into mechanical work, for example for operating a generator installation (not shown), or a fuel cell installation, in which the oxidation reaction is used directly for electrical power generation E2.

Such a drive device C11 comprises a closed cycle, that is to say it causes no emissions into atmosphere. The oxidation gases M27 occurring during performance of the mechanical work, which contain essentially only carbon dioxide and if applicable also water, are post-treated C12, compressed C13, and the remaining residual gas M26 is fed back into the cycle of the utilization installation AB.

If the utilization installation A and the peak load energy installation C are situated at the same site, the residual gas M26 can be fed back directly. In an advantageous variant, a temporary storage BB is provided, as shown in FIG. 4. As already described above, the energy installation C of the facility Z according to the invention can be arranged separately from the utilization installation A.

The oxidation reaction generating thermal or electrical energy takes place in the drive device C11 using pure oxygen M31 instead of air. The use of oxygen M31 instead of air avoids, firstly, owing to the absence of atmospheric nitrogen in a thermochemical reaction at high temperatures, the formation of nitrogen oxides; especially, however, essentially only carbon dioxide and water vapor remain in the occurring oxidation gases M27. Depending on the stoichiometry of the reaction, the gases occurring can also contain certain fractions of carbon monoxide and unreacted fuel. These can likewise be fed in without problems into the cycle of the utilization installation A.

The reaction products M27 of the energy-generating oxidation reaction are essentially gaseous. The corresponding oxidation gas mixture is then compressed C13 in order to reduce the volume. Using a heat exchanger C12, the oxidation gas mixture M27 can be cooled upstream and/or downstream of the compression. Water M41 is condensed out and separated off, whereby only carbon dioxide remains in the residual gas M26, if applicable having fractions of carbon monoxide and unreacted fuel. The residual gas M26 is then fed to the first process stage P1 of the utilization unit AB of the installation A, and so a closed material cycle results. Alternatively, the residual gas M26 can also be fed into the second process stage P2, or the third process stage P3, which is indicated in FIG. 4 by dashed arrows.

Thus it is possible that in a facility Z according to the invention, liquid or gaseous hydrocarbons and hydrocarbon derivatives are generated from carbonaceous materials M11, and the resultant high-grade fuel mixture M61 is subsequently converted into electrical energy E2. The carbon dioxide produced is fed back and is in part or completely converted back to fuel M61 in the utilization installation A. In this manner, the effective carbon dioxide discharge of the peak load generator installation C can be very greatly reduced or even entirely avoided.

The drive device can also be operated without problems in combined operation with hydrogen M32 as a further fuel. In such a case, the hydrogen fraction leads to a reduction of the residual gas amount M26 occurring downstream of the heat exchanger/condenser and compressor, since only water arises in the oxidation of hydrogen with oxygen.

Further possible embodiments of suitable drive devices for an energy installation will be discussed later in FIGS. 13 to 15.

Figure 5:
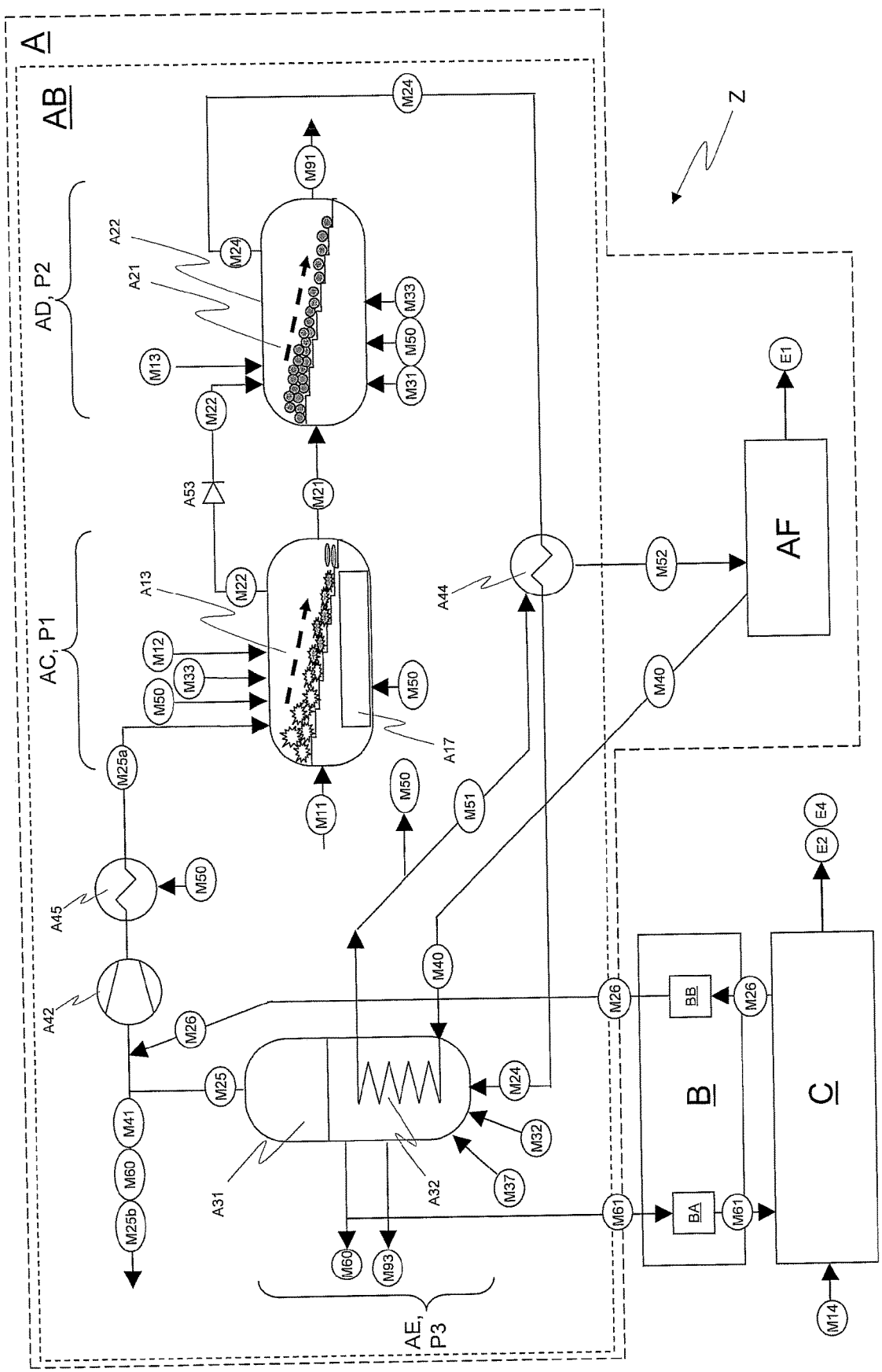
FIG. 5 schematically shows a possible embodiment of a facility according to the invention with a utilization installation having a base load energy unit, and a peak load energy installation.

Another advantageous embodiment of a facility Z according to the invention is shown in FIG. 5. This comprises, in addition to the utilization unit AB, both a base load energy unit AF, and a peak load energy installation C.

In a further advantageous variant of a utilization process according to the invention, chemical energy is introduced into the process in the form of molecular hydrogen in relatively large amounts. Such an embodiment of a facility Z according to the invention is shown, for example, schematically in FIG. 6(a). The utilization installation A receives material in the form of carbonaceous starting materials M10 as has already been described above. Carbon dioxide M33 is likewise suitable as carbon source. The primary energy source used in the shown embodiment is mainly the chemical energy of the molecular hydrogen M32. On one hand the hydrogen serves for the reduction of the starting material, and secondly the oxidation with oxygen leads to the supply of thermal energy.

Molecular hydrogen M32 may be produced from water by electrolysis, wherein also molecular oxygen M31 accumulates. Electrical energy E1 can be converted in this manner into chemical energy. The gaseous molecular hydrogen, however, has a considerably lower energy density compared with liquid fuels, but also compared with gaseous hydrocarbons, as a result of which it has not yet been able to establish itself for use as propellant for vehicles.

In a utilization process according to the invention, the chemical energy of hydrogen can be converted efficiently into chemical energy in the form of high-value hydrocarbons and other products. Advantageously, the oxygen M31 occurring during the electrolysis is also used in order to introduce all of the occurring chemical energy into the process, or a maximum of the electrical energy put into the electrolysis, respectively.

In the shown example an installation D provides molecular hydrogen M32 and oxygen M31. The electrical energy E3 for the electrolysis reaction originates preferably from regenerative energy sources (wind power, solar energy, water power etc.). This has the great advantage that an inherent disadvantage of wind power installations DA and solar energy installations DB can be overcome, namely the cyclic, and due to the dependence on external factors not always guaranteed, energy generation. This leads to correspondingly low achievable market prices for the generated electrical energy. By conversion into chemical energy (molecular hydrogen M32 and oxygen M31) in contrast, the generated energy output can be temporarily stored. The hydrogen, and, if possible, also the oxygen, is then utilized in a process according to the invention, in order to produce for example more readily manageable liquid fuels that have a higher energy density, or other high-value products.

The energy of the energy generation units DA, DB of the installation D is transported in the form of electrical current to the electrolysis unit DC, which is located at the place of the utilization installation A, and in which then hydrogen M32 and oxygen M31 are generated locally. Part of the oxygen is not needed and can be utilized in other ways, for example in a energy installation C of the facility Z according to the invention. Temporary storages DE, DF, for example in the form of pressure tanks, serve as buffers for compensating for the fluctuating energy generation of the energy generation units DA, DB.

As already explained above, the utilization installation A produces high-value hydrocarbons and other synthesis products M60, and, as the case may be, energy E1. Residues M90 are continuously removed from the system. Likewise, water can easily be removed from the system, for example by condensation M41. In the shown exemplary embodiment, water mainly serves as oxidizing agent and gasification agent, if no oxygen is available. Water M41 removed from the system, however, also serves as a sink for oxygen. This is mainly relevant when the system takes up large amounts of carbon dioxide M33 as carbon source.

In a combination as shown in FIG. 6(a), a utilization process according to the invention can also produce high-value and energy-rich hydrocarbon products M60 from comparatively low-energy carbon sources. In an extreme case, the process can in principle even be carried out exclusively using pure carbon dioxide as carbon source. Since the supplied electrical energy originates directly or indirectly (wind power, water power) from the sun, then results—seen from a principal standpoint—artificial photosynthesis, namely generating carbon compounds from carbon dioxide, water and sunlight.

The combination of the utilization installation A with an energy installation C is facultative.

In case the location of the regenerative energy is too far away, it can be more efficient to transport locally produced hydrogen M32 to the utilization installation, instead of the electrical current. Such a variant is for example shown in FIG. 6(b). Energy E3 is generated in energy generating units DA, DB that are farer away, from which then molecular hydrogen M32 is produced in an electrolysis unit DC. This molecular hydrogen is stored in a temporary storage DE, and is brought in suitable transport means DG to the utilization installation A. Hydrogen produced as a by-product in the chemical industry can serve as a further source of molecular hydrogen M32.

The difference in the power spectrum of a facility Z according to the invention compared with a conventional power station operated with carbonaceous fuels is explained more precisely in FIGS. 7(a) to (d).

Figure 7:
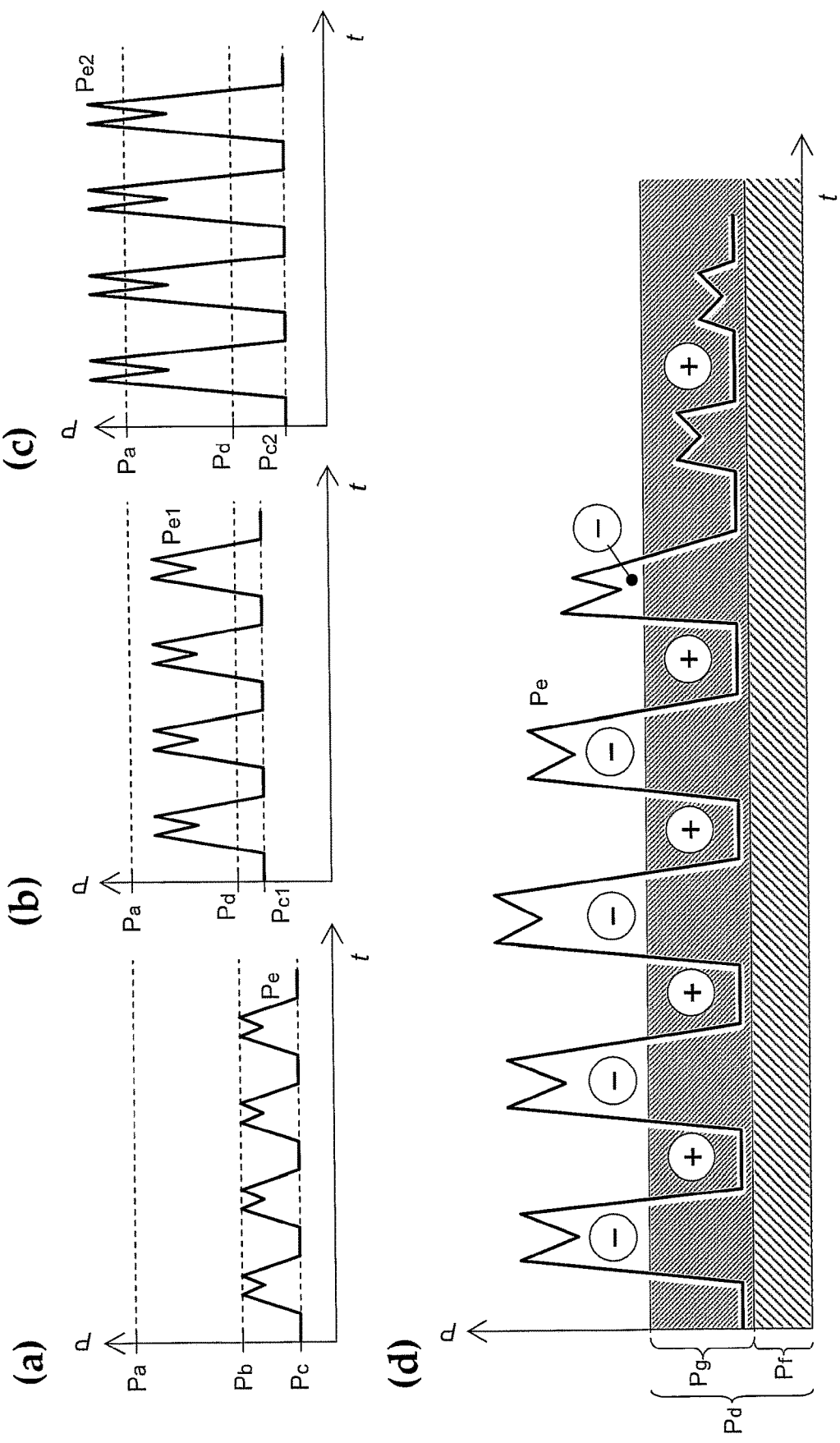
FIG. 7 schematically shows the power profile (a) of a conventional thermal power plant installation, (b), (c) a facility according to the invention, and (d) peak load and base load profiles of a facility according to the invention.

FIG. 7(a) schematically shows the power profile of a conventional thermal power station. The vertical axis shows the power P and the horizontal axis the time t. The power station has an added heat content $P_a$, that is to say the heat energy or power contained in the fuel as chemical energy, and an effective thermal power $P_b$, that is to say the heat energy that is effectively convertible into electrical or mechanical energy per time unit. The demand for electrical power $P_e$ in a conventional power grid varies not only during the day but also during the week. In order to be able to cover with a power station also the peak loads, in addition to the base load $P_c$, the entire nominal output of such a power plant installation must be directed towards the peak load. This means that due to the required peak performance the dimensioning of the installation is larger than would actually be necessary on the basis of the average total power.

In a facility according to the invention for the generation of energy, in contrast, this is not necessary. Such a facility Z, as is shown for example in FIG. 1, converts in the utilization installation A a constant part of the chemical energy supplied in the form of the carbonaceous materials M10, M11 into thermal energy in the form of steam, which then is converted for example using a steam turbine of the base load energy unit AF into electrical energy $P_f$. A further fraction of the chemical energy supplied in the form of the carbonaceous materials M10, M11 is converted in the synthesis stage P3 of the utilization unit AB with a constant production power $P_g$ into chemical energy in the form of high-value carbonaceous fuels M61, for example diesel-like products or gaseous products such as propane. These fuels can be stored BA in any desired amount and/or, as shown in FIG. 2, transported over short or longer distances.

FIG. 7(d) schematically shows the profile of the total power $P_e$ of a facility according to the invention over the course of a week. During the peak load demand during the working days the peak load energy installation C generates electrical energy from the chemical fuels M61, which can then be fed at a correspondingly high price into an energy grid. The demand for chemical fuels M61 exceeds in this case the production power $P_g$ of the utilization installation A substantially, which is marked by (−). This above-average consumption is taken off from the fuel storage BA. During the night and at the weekend the demand is greatly reduced, and the production power $P_g$ exceeds the demand $P_e$, which is marked by (+). As a consequence, the fuel storage BA is replenished again.

During the base load periods, the energy installation C can be run down to a minimum power level, as shown in FIG. 7(d), or the energy installation C is shut down completely, and so the base load $P_c$ is completely covered by the base load energy unit AF.

A facility according to the invention therefore has the substantial advantage that only a part $P_f$ of the constant effective power $P_d$ occurs in the form of thermal power, which as in a conventional power station must be converted immediately into electrical and/or mechanical energy. This part $P_f$ can be used for delivering the power for the base load minimum $P_c$. Another part $P_g$ of the effective power $P_d$, on the other hand, is temporarily stored in the form of fuels M61 in the storage BA. The demand $(P_e-P_f)$ that exceeds the thermal power of the base load energy unit AF can then be covered by the peak load energy installation C from the fuel storage BA. This allows a facility according to the invention to be designed in such a way that the effective power $P_d$ composed of thermal power $P_f$ of base load energy unit AF and production power of the synthesis stage P3 of the utilization unit AB corresponds to the mean average demand as shown in FIG. 7(b). As a result, in a facility according to the invention having the same effective thermal power $P_d$ as the thermal power $P_b$ of a conventional power plant installation, a comparatively higher base load power $P_{c1}$ and a higher peak load power is achieved, wherein for a short time the peak power can considerably exceed the effective thermal power $P_d$.

Considered the other way round, a facility Z according to the invention, in order to be able to cover a defined demand profile, can be designed having a considerably smaller installed thermal power, for example with 75% or 50% of the thermal power of a comparable conventional power station. This leads to considerably lower capital costs.

A facility according to the invention can be designed and optimized in such a way that the power $P_f$ generated directly from thermal energy is reduced in favor of the power $P_g$ generated from the fuels M61. Such a variant is shown in FIG. 7(c). Such a facility according to the invention can, while covering a reduced base load minimum $P_{c2}$, store a significantly higher amount of energy. The corresponding stored energy can finally be used for generating peak load power $P_{e2}$, which can then be sold at a higher price.

Depending on the circumstances, it is possible to optimize a facility according to the invention in regard to the flexible generation of peak load energy to the extent that the base load power of the energy AF is minimal, and optionally may only be sufficient for covering the internal energy demand of the facility.

Utilization Processes and Utilization Installations

Figure 8:
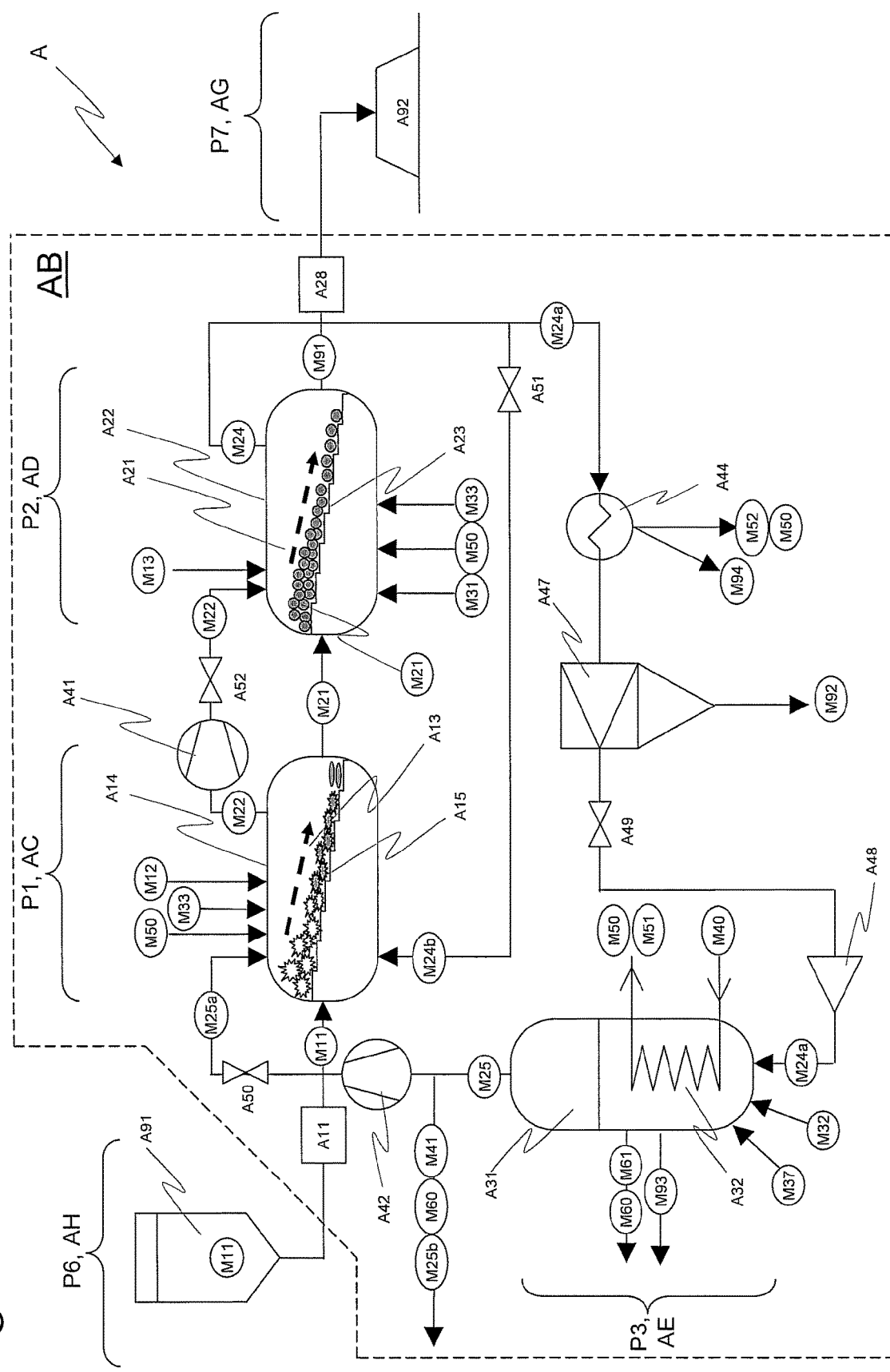
FIGS. 8 to 12 schematically show various possible exemplary embodiments of utilization installations for a facility according to the invention.

A first possible variant of a configuration of an installation A for the thermal-chemical utilization of carbonaceous solids using a process according to the invention, and a facility according to the invention, respectively, is schematically shown in FIG. 8. The utilization installation A of the facility Z according to the invention comprises a utilization unit AB with three subunits AC, AD, AE for carrying out the three process stages P1, P2, P3 of the process according to the invention, which are connected to form a closed cycle in such a manner that they allow a closed, cyclic gas stream. Of the treatment unit AH, only the silo A91 for the provision of the carbonaceous material M11 treated for the process is shown. Of the discharging unit AG, on the other hand, only the slag depot A92 is depicted. The utilization installation A can comprise an energy unit (not shown) or not. This is not relevant for the functionality of the utilization process.

The three subunits AC, AD, AE of the utilization unit AB are connected to a closed cycle in such a way that they allow a closed, cyclic gas stream. In the first process stage P1 (pyrolysis stage), and the first subunit AC, respectively, carbonaceous starting material M11 is pyrolysed under pressure, thereby forming pyrolysis coke M21 and pyrolysis gases M22. In the second process stage P2 (gasification stage), and the second subunit AD, respectively, pyrolysis coke M21 is gasified to form synthesis gas M24, which is finally reacted in a third process stage P3 (synthesis stage), and in the third subunit AE, respectively, to form hydrocarbons and/or solid, liquid or gaseous products M60.

The carbonaceous starting materials M11 that are to be processed are fed into the cycle continuously from a supply facility AH, P6 via the first process stage P1. Simultaneously, the products M60, M61 generated from the synthesis gas M24 are continuously drawn off from the third process stage P3. The various residues M91, M92, M93 are continually removed from the cycle.

A multiplicity of carbonaceous materials can be used as starting material M11 for a utilization process according to the invention, in particular waste, biomass, coal, or other heterogeneous materials such as for example contaminated soil, but also previously deposited waste, for example from landfills. This allows an environmentally friendly and cost-efficient removal of open landfills. Also solid-liquid petroleum-containing materials that are difficult to utilize, such as oil shale, oil sand or oil sludge, can be utilized in a process according to the invention. Gaseous carbonaceous by-products of the chemical industry or the petroleum industry, which otherwise could not be utilized and may even have to be flared off, can also be used as additives M12.

The calorific value of the starting materials, the carbon content, water content, and the content of non-combustible residues such as metal, glass and ceramics, can vary very much. For that purpose the starting material can be comminuted to a piece size suitable for a certain utilization installation, wherein the preferred piece size results from the consistency of the material and from the specific design of the first pressure reactor, and the internal transport system in the reactor, respectively. For processing using a moving grate, for example, a piece size of approximately 5-10 cm is very suitable.

The first process stage P1 comprises in the shown example a first pressure reactor A13, in which under pressure a pyrolysis of the carbonaceous starting material M11 takes place. The starting material M11 is conveyed into the pressurized pyrolysis reactor A13 via a suitable pressure lock A11. In the shown embodiment, the pyrolysis reactor A13 consists of a horizontal pressure body A14 in which the horizontal transport of the lumpy material proceeds along the reactor during pyrolysis via a schematically shown moving grate A15, with grate plates moving to and fro. Any other transport device suitable for continuous advancing of the starting material that is to be processed is likewise useable, for example roller grates, chain conveyors, conveyor screws, etc. A rotary kiln furnace can also be used.

In the pyrolysis reactor A13 the material is transported continuously through the pressure reactor A13 at a temperature of approximately 300-800° C. and a pressure of 1-60 bar and in the course of this is pyrolysed in the absence of oxygen. The temperature is selected, inter alia, in such a manner that in addition to maintaining the pyrolysis reaction, the desired operating pressure is maintained, firstly, owing to the expansion of the gases because of the temperature, and secondly owing to the new production of pyrolysis gases. A minimum temperature of 450° C. ensures continuous complete reaction of free oxygen compounds during the pyrolysis. An operating temperature of 500-600° C. and an operating pressure between 5 and 25 bar are particularly well suited.

The thermal energy necessary for the pyrolysis reactions originates firstly from the hot feedback gas stream M24$b$ from the second reactor A21, which will be considered further hereinafter. In addition, process steam M50 serves for maintaining the operating temperature of the first reactor. An external heat supply such as, for example, a heat exchanger or an external heater can likewise be present. The latter is also advantageous during startup of the utilization installation A from the cold state.

Recycle gas M25 from the third process stage (synthesis stage) P3 is fed to the first pressure reactor A13 after passage through a compressor A42. The recycle gas M25 mainly contains carbon dioxide, and also water vapor, and carbon monoxide and hydrogen that have not reacted in the synthesis stage, and also residual contents of low-molecular-weight hydrocarbons. In order to be able to control the process, additional carbon having a high calorific value can be introduced into the reactor A13, for example in the form of coal or heavy oil. These additives M12 can already be added in advance to the starting material M11, or be introduced separately into the reactor A13. The mixing of viscous additives M12 with solid starting material M11 facilitates the transport of viscous material within the reactor. Liquid additives M12 in addition increase the amount of pyrolysis gas, and thereby the operating pressure.

In the pyrolysis in the first process stage P1, pyrolysis coke M21 forms, which essentially consists of solid carbon and inorganic residues. The pyrolysis coke M21 is discharged at the end of the pressure reactor A13. The pyrolysis gases M22 forming during the pyrolysis do not only contain gaseous materials, but also materials that are solid and liquid at room temperature. The composition of the pyrolysis gases M22 naturally depends greatly on the starting materials, and may also contain pollutants.

The pyrolysis coke M21 is transported under pressure into the pressure reactor A21 of the second process stage P2. A closed conveying screw, for example, is again suitable. A pressure lock can also be provided. The pyrolysis gases M22 are likewise transported via a separate transport pipe into the second pressure reactor A21. A compressor A41 arranged in the transport pipe conveys the pyrolysis gases into the second pressure reactor A21, which is at a higher operating pressure.

In the second process stage P2, the operating temperature is between 600 and 1600° C. In this second process stage the solid carbon in the pyrolysis coke M21 is then gasified using carbon dioxide and if appropriate oxygen and/or steam as gasification agent, to form carbon monoxide and hydrogen, according to the reactions I, II and III.

The carbon dioxide originates primarily from the recycle gas M25. Additional carbon dioxide M33 can also be fed into the cycle. The water vapor consists primarily of the residual moisture of the starting material M11. Process steam M50 can also be fed in.

The thermal energy necessary for the course of these endothermic pyrolysis reactions originates, for example, from a partial oxidation of the solid carbon (reaction III) with oxygen M31 passed into the second pressure reactor A21. The exothermic water gas shift reaction IV can also contribute thereto.

For starting the utilization installation A, and for controlling the process, it can be necessary to feed additional fuels M13 to the second reactor A21, such as, for example, coke, oil or petroleum gas, and/or to increase the oxygen supply in order to temporarily increase the heat generation.

The ratio between carbon monoxide and hydrogen, which is of importance for the later synthesis in the third process stage P3, is given by the water gas shift reaction IV and can be influenced in the direction towards the right-hand side by adding process steam M50. However, it is advantageous to keep the total amount of water in the system as low as possible, and to introduce additional hydrogen M32 directly into the third process stage instead.

In the shown example of a utilization unit AB, the second process stage likewise comprises a pressure body A22, in which the pyrolysis coke is transported within the reactor A21 by a moving grate A23. Again, other transport systems are also possible, as they have already been discussed for the first pressure reactor A13. This has the advantage that the pyrolysis coke can be processed without further preparation in the second process stage.

In principle, the second reactor can alternatively be designed differently. For example, the pyrolysis coke could be comminuted or milled in advance, which then allows a gasification of the coke in a fluidized stream or entrained stream. However, this variant has the disadvantage that the particles have a shorter retention time in the reactor, which requires a more homogeneous material feed and preparation. In addition, such installations require a more precise and more rapid control of the gas stream velocity and of other process parameters.

The reactive surface of lumpy pyrolysis coke is comparatively small compared with a likewise possible reaction in the fluidized stream, which, however, is compensated for by the comparatively long residence time in the reactor A21 owing to the high mass capacity of the pressure reactor. A further advantage is the simpler upscalability. By means of a simple elongation of the pressure reactor or an enlargement of the cross section, the capacity and therefore the conversion rate can be increased without the need of changing the relevant process parameters such as pressure or temperature. Reactors having an entrained stream or fluidized stream, in contrast, cannot be scaled up in such a simple and problem-free manner.

The oxygen M31 necessary for the partial oxidation and, if appropriate, the process steam M50 is blown into the firebed formed by the pyrolysis coke, whereby the necessary thermal energy is generated and the reactor A21 is kept at operating temperature. Instead of pure oxygen, air could also be used, wherein, however, the inert atmospheric nitrogen expands the gas material stream circulating within the utilization installation and is difficult to remove again. This considerably reduces the efficiency of the installation and so pure oxygen is to be preferred in any case. In addition, the absence of nitrogen in the system also prevents the formation of nitrogen oxides.

In the exemplary embodiment of a utilization installation A shown in FIG. 8, the pyrolysis gases M22 are blown into the gas phase above the firebed in the pressure reactor A21, where at the prevailing high temperatures the polyatomic molecules contained in the pyrolysis gases M22 are very rapidly cracked and broken down. The synthesis gas M24 formed in the second process stage therefore essentially no longer contains organic molecules, and can be used for the Fischer-Tropsch synthesis in the third process stage. Also, pollutants such as dioxin, for example, are decomposed.

The oxygen supply M31 into the firebed and the point of entry of the pyrolysis gases M22 into the pressure reactor are advantageously chosen in such a manner that dioxins cannot form, which can be achieved by a suitable spatial separation. Likewise, in the exiting synthesis gas, no oxygen should be present.

For unproblematic starting materials such as, for example, woodchips or straw or other unpolluted biomasses, it is also possible to burn the pyrolysis gases M22 in advance with oxygen in a separate burner and to pass the hot exhaust gases likewise into the firebed, for the purpose of feeding thermal energy, or to blow them unburned directly into the firebed where they are also oxidized.

At the end of the pressure reactor A21, residues remain in the form of ash and inert residues, and as the case may be unprocessed carbon. If slagging is desired, additives can be added that lower the ash melting point. For this purpose, for example chalk powder can be added to the starting material M11. The slag is discharged from the second pressure reactor A21 via a suitable pressure lock A28 from the pressure area of the utilization installation AB.

The second process stage can alternatively be designed in such a way that unreacted pyrolysis coke at the end of the pressure reactor is again transported to the start and thus can pass through the reactor a second time. This allows a shorter design of the pressure reactor.

The synthesis gas stream M24 is discharged from the second pressure reactor A21, and a major part M24a is passed through a suitable heat exchanger A44, where the gas stream is cooled down to a temperature that is suitable for the Fischer-Tropsch synthesis in the third process stage P3, at the same time generating e.g. process steam M50 for internal process purposes and/or steam M52 for energy generation in an energy unit AF (not shown). Due to the lower temperatures, pressure falls and the equilibrium of reactions I, II and IV is shifted, as a result of which the fraction of carbon dioxide in the synthesis gas increases again. Likewise, solid carbon M94 can separate from the gas stream in the form of graphite. The carbon M94 can be passed as starting material M11, M12 back into the cycle, be used as a valuable material in other ways, or be removed from the system as residual material.

Subsequently the synthesis gas stream M24a is passed into a cyclone separator A47, where dust M92, mainly consisting of residual coke and ash, is separated off. The residual dust M92 can be passed back into the first pressure reactor A13 or the second pressure reactor A21, or it is treated and/or discharged. Instead of a cyclone separator, also other suitable gas stream purification devices can be used.

If the carbon M94 is not separated out, it arrives together with the synthesis gas stream in the Fischer-Tropsch reactor A31, where it can be separated out or filtered off together with the carbon formed as by-product in the Fischer-Tropsch reaction.

Depending on the starting material, further a gas stream treatment can be provided, in order to remove interfering materials in the synthesis gas. In particular, residues are advantageously removed that are disadvantageous to the subsequent synthesis stage. For example, sulphur compounds can act as a catalyst poison in the Fischer-Tropsch synthesis.

The synthesis gas M24 is then fed via a pressure regulator A48 to a third pressure reactor A31 of the third process stage P3, in which a Fischer-Tropsch synthesis is carried out. The pressure regulator A48 reduces the pressure to the value desired for the third process stage. For setting the desired ratio of carbon monoxide/hydrogen, additional hydrogen M32 can be passed into the Fischer-Tropsch reactor A31. Likewise, the necessary solid catalysts M37 are supplied.

In the Fischer-Tropsch synthesis of the third process stage, the carbon monoxide and the hydrogen react highly exothermically (approximately 158 kJ/mol per hydrocarbon chain member at 250° C.) in the presence of heterogeneous catalysts (for example iron, cobalt, ruthenium, nickel catalysts) to form alkanes, olefins, alcohols, aldehydes and other hydrocarbon compounds and derivatives. By-products are methane and solid carbon, which are likewise formed in highly exothermic reactions. The exact parameters of the Fischer-Tropsch synthesis, in particular pressure and temperature, primarily depend on the products to be produced, and are not directly relevant to the fundamental functional principle of a facility according to the invention or the process according to the invention. Higher process temperatures have a tendency to lead to shorter chain lengths and increased carbon deposition, whereas higher pressures lead to longer chain lengths. In addition, especially the present partial pressures of carbon monoxide, hydrogen and water have a great influence on the synthesis products.

Suitable for the synthesis process stage are, for example, low-temperature Fischer-Tropsch processes, which are operated, for example, at 210 to 250° C., and mainly yield diesel-like products and long-chain fractions in the form of waxes. The latter can then be utilized further, for example by hydrocracking. High-temperature processes having temperatures between 320 and 350° C. in turn yield considerable fractions of methane, short-chain alkanes and alkenes, and also relatively high fractions of light petrol. For low-temperature processes, for example tube-bundle reactors are suitable, in which the synthesis gas flows from top to bottom through catalyst-charged, cooled tubes. Recycle gas and products leave the tube at the bottom.

Particularly suitable reactors are modern suspensation reactors (schematically shown in FIG. 8), in which the solid catalyst floats finely distributed in the liquid product (so called Sasol-slurry Fischer-Tropsch process). Reaction products are separated off from the liquid phase, while gaseous products leave the reactor as part of the recycle gas M25. The heat is removed via suspended cooling tubes A32, thereby generating steam M51, M50.

Suspensation reactors have a simpler form of construction than tube-bundle reactors, and are therefore less costly. The catalyst can be used more efficiently and is exchangeable during running operation, which is advantageous in the cyclic process according to the invention. In addition, such a process has the advantage that the heterogeneous catalyst can be continuously regenerated by mechanical exposure of new unused surfaces of the catalyst particles during the circulation. In this manner sulphur poisoning of the catalyst can be continuously compensated for. As a consequence thereof, if appropriate, the removal of sulphur from the synthesis gas stream can be dispensed with.

The steam M51, M50 obtained by the cooling device A32 contains considerable thermal energy, but is not yet hot enough for efficient utilization, for example in a steam turbine of an energy unit AF. It is therefore advantageously used for the production of hot steam M52, for example in the heat exchanger A44, in order to increase the general energy efficiency of the installation. The interplay between a utilization unit AB and a further energy-generating subunit AF of a utilization installation A has already been considered in FIGS. 3 to 5.

The gas stream M25 which leaves the Fischer-Tropsch reactor A31, in addition to unreacted carbon monoxide and hydrogen gas, further contains water vapor, carbon dioxide and gaseous reaction products M60. A fraction of highly volatile hydrocarbons M60 can be condensed out therefrom, for example using a cooling column (not shown). Likewise, water M41 can be condensed out, and thus removed from the recycle gas and thereby from the material stream. From the remaining recycle gas stream, a part M25b can be separated off as process product. The remaining recycle gas stream M25a is compressed in a compressor A42, and is recirculated to the first reactor A13.

The cyclic conveying of the gas stream within the utilization installation A proceeds mainly owing to the prevailing pressure differentials along the cycle. These are primarily generated by the two compressors A41, A42. Depending on the design of the installation, one of the two compressors can be dispensed with, which lowers the total costs of the installation. If the installation contains only one compressor (such as, for example, in the second exemplary embodiment of a utilization installation in FIG. 9 described hereinafter), the arrangement upstream of the first reactor A13 has the advantage that the corresponding compressor A42 needs to compress a lower gas volume than a compressor A41 between the first and second process stages, where in addition the pyrolysis gases accrue, and the total volume is higher owing to the higher temperature, or even between the second and third process stage.

If the compressor A41 is dispensed with, there is only a small pressure drop between the two reactors A13, A21, such that the first and second process stages proceed essentially at the same pressure. The gas stream then runs from the compressor A42 via the first reactor A13, second reactor A21 and third reactor A31 back to the compressor A42. If, in contrast, the compressor A42 is dispensed with, the pressure is essentially identical within the third reactor A31 and the first reactor A13. A compressor can also be arranged between the second and third process stage. For reasons of entropy, at least one compressor or another transport means must be present in order to convey the gas stream and to keep the process running.

For compensating temporary fluctuations in the gas production owing to heterogeneous starting material, pressure storages (not shown) can be provided along the gas cycle M22, M24, M25. Similarly, it is also possible to provide a temporary storage for the pyrolysis coke M21.

If the utilization unit A of FIG. 8 is dimensioned comparably small, and correspondingly the volumetric flow rate M22 between the first pressure reactor A13 and the second pressure reactor A21 is comparatively small, the compressor A41 can generate a pressure difference of several bar with reasonable energy expenditure. The first process stage could then be run at a substantially lower pressure than the second process stage. The first process stage can even be carried out at atmospheric pressure or even reduced pressure.

Start of Operation of a Utilization Installation

Hereinafter a possible method will now be described for starting the operation of a utilization installation A as shown in FIG. 8. For starting up of the utilization installation A, the cycle and the three process stages are flushed and filled with an oxygen-free gas, advantageously with carbon dioxide and/or carbon monoxide and/or hydrogen gas or mixtures thereof, that is to say synthesis gas. Subsequently the second reactor A21, filled in advance with coke, is then heated up, for example using gas burners. For this purpose the second reactor is separated from the cycle, by closing the corresponding connections. During the heating up to the desired operating temperature, the transportation A23 of the coke within the pressure reactor A21 is not yet activated. If appropriate, a temporary bypass (not shown) can be provided in the cycle, between heat exchanger A44 and pressure reactor A21, in order to be able to circulate the heated gas in the system and to evenly heat up the entire installation section. The pressure is likewise increased to the scheduled value.

In parallel thereto, the first pressure reactor A13, which has also been filled with coke in advance, is separated from the cycle and heated up to the intended operating temperature of the first process stage. The pressure is likewise brought to the desired value for the first process stage. The material transport A15 in the first reactor still remains switched off. However, the heating should preferably take place without starting material, since pyrolysis of the starting material below a minimum safe operating temperature of 450° C. can lead to the formation of explosive mixtures. The coke, in contrast, is already pyrolysed, and only serves for feeding coke into the second process stage, when later the cycle is started up.

The Fischer-Tropsch reactor A31 is likewise run up to the operating conditions while being separated from the cycle. After the operating conditions have been reached in the various process stages of the utilization installation, the various transport systems A15, A23 are run up slowly, the cycle is opened and the compressors A41, A42 are activated, so that finally an equilibrium state of the utilization installation AB results at the desired operating parameters.

Figure 9:
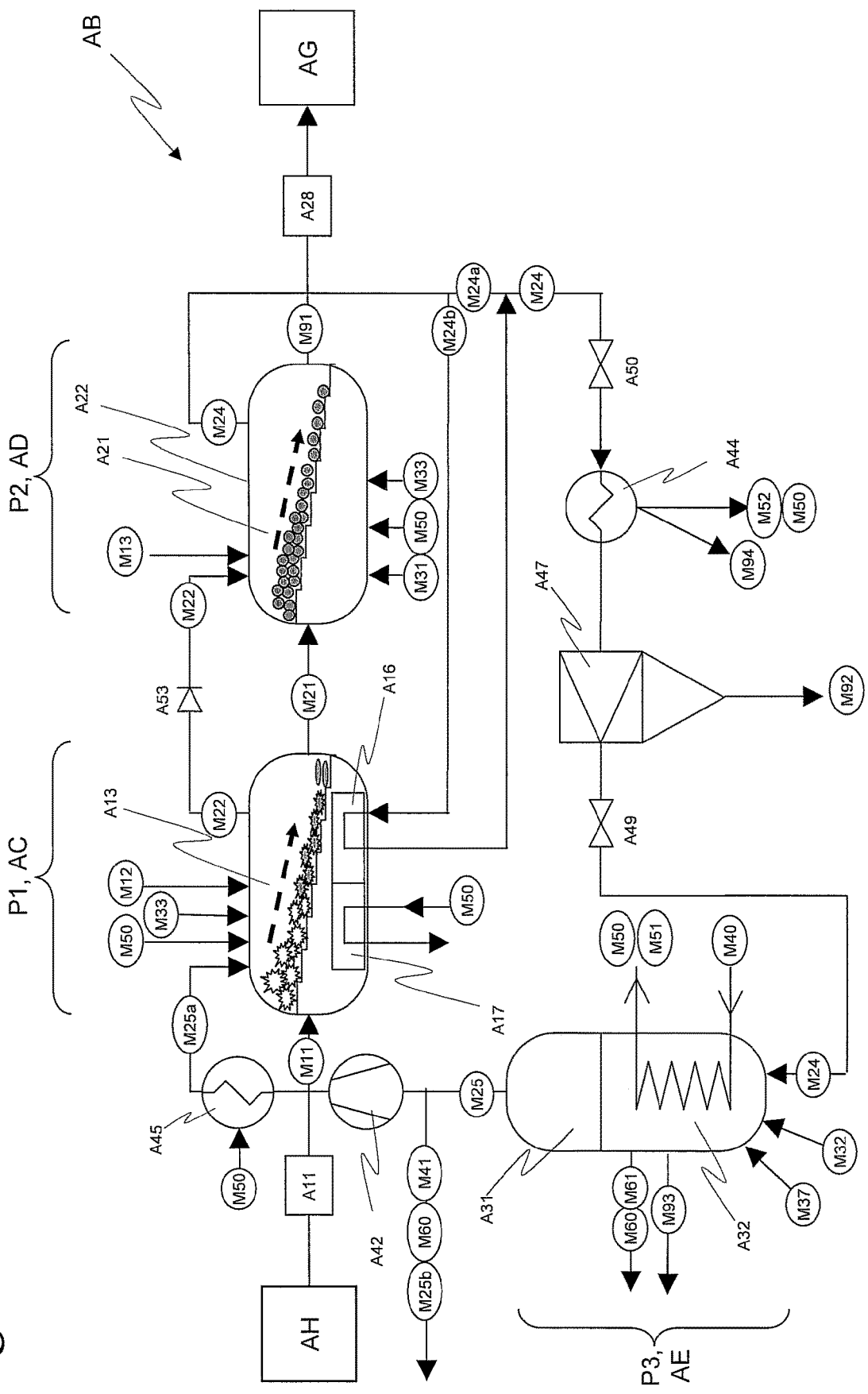

A further embodiment of a utilization unit AB of a facility Z according to the invention is shown in FIG. 9. For the sake of clarity, the boundary of the utilization unit AB is not shown.

In contrast to the utilization unit AB in FIG. 8, no compressor is arranged between the first pressure reactor A13 and the second pressure reactor A21, but only a nonreturn valve A53, which, however, can also be dispensed with. The gas stream is conveyed through the installation by the pressure drop generated by the compressor A42. Since this advantageous variant needs only a single compressor A42 that, in addition, can have a lower throughput volume, the overall costs of the installation AB are reduced.

In the shown variant, the branched-off synthesis gas stream M24b is not passed directly back into the first reactor A13, but instead is conducted through a heating device A16 of the pressure reactor A13, and is then again combined with the synthesis gas M24a. Alternatively or in addition, a further heating device A17 can be provided, which is operated with process steam M50.

A heat exchanger A45 is arranged in the recycle gas stream M25a, and serves for heating the recycle gas stream M25a by process steam M50. The recycle gas stream thus in this embodiment also serves as the heat supply to the first pressure reactor A13.

In the shown example, no pressure reduction is provided upstream of the third pressure reactor A31. The pressure in the third process stage is controlled in this case directly by the pressure control in the second process stage, and by the subsequent pressure drop owing to the cooling down of the synthesis gas stream M24 in the heat exchanger A44, and by the compressor A42.

In a further possible variant of the process according to the invention, the low-temperature Fischer-Tropsch reactor of the third process stage is replaced by a high-temperature Fischer-Tropsch reactor, in which the catalyst is present as swirled flydust. The gaseous short-chain hydrocarbons that are preferentially formed in the high-temperature Fischer-Tropsch synthesis, and which after a first condensation stage remain in the recycle gas, are separated off by permeation gas filters from the smaller molecules of the recycle gas such as carbon dioxide, carbon monoxide, hydrogen. Such systems are known, for example, from the petrochemical industry for purifying petroleum gas. In the present case they serve for generating a first hydrocarbon-rich gas phase and a second, low-hydrocarbon gas phase. The hydrocarbon-rich gas phase is further utilized as fuel for a second generator stage for generating electrical energy, or is processed to liquid gas and petroleum gas. The low-hydrocarbon and carbon dioxide-rich second gas phase is charged back into the cycle as recycle gas.

In yet another variant of a utilization installation of a facility according to the invention, the third process stage P3, instead of a Fischer-Tropsch reactor, contains a liquid-phase methanol synthesis reactor. The liquid-phase methanol synthesis known from the prior art is particularly suitable for producing methanol in high yield from synthesis gas having a relatively high fraction of carbon dioxide. The synthesis takes place in a "slurry-bubble column reactor" in which the synthesis gas is blown into a slurry of the pulverulent catalyst in an inert mineral oil. The reaction is highly exothermic and so a cooling device is necessary. The produced gaseous methanol leaves the pressure reactor together with unreacted synthesis gas. After entrained mineral oil and catalyst are separated off, the methanol is condensed out.

Methanol is a valuable base product for the chemical industry and can also be used as a propellant. Methanol can, in addition, act as additive to petrol, wherein, for example in Germany a fraction of up to 3% methanol in vehicle petrol is permitted. The methanol can in particular also be used as fuel M60 for a second generator stage.

Control and Optimization of the Operating Parameters of a Utilization Installation The process according to the invention shown in FIGS. 8 and 9 is based on a cyclic matter flow through the three process stages P1, P2, P3 of the utilization unit AB, wherein carbonaceous starting material M11 is fed into the cycle as carbon source and energy source, and the products of the synthesis stage are branched off as high-grade products M60 or as fuels M61 for the energy installation C of the facility Z according to the invention. Slag M91 and other residual materials M92, M93, M94, as well as water vapor in the recycle gas M25b, are continuously removed from the cycle. The steam produced in the heat exchangers is used on one hand as process steam M50 for operating the installation, thereby increasing the efficiency and effectiveness of the installation. On the other hand, the superheated steam M51, M52 can be used for energy generation in an energy unit AF.

Essentially, in a utilization process according to the invention, from an energy-rich but heterogeneous solid starting material M11 that is difficult to utilize, an again energy-rich product M60, M61 is produced, namely the different fractions of the Fischer-Tropsch stage. These subsequently can be further utilized, for example as liquid propellants or as reactants for the chemical industry. The energy necessary for operating the utilization installation AB originates from the partial oxidation reaction in the second process stage, wherein an excess of the chemical energy generated (in the form of the synthesis gas) is later converted again in the exothermic Fischer-Tropsch reaction of the third process stage into thermal energy in the form of steam M50, M51.

In a particularly advantageous variant of an energy generation process according to the invention, or a facility Z according to the invention, respectively, superheated steam M52 is generated from the starting material M11, for long-term operation of a base load energy unit AF, and also fuel M61 for flexible operation of a peak load energy unit C.

Owing to the closed, circulating matter stream in the process, a dynamic equilibrium is present during operation of the utilization installation A. The necessary values of the various parameters (pressure, temperature, chemical compositions, transport velocities etc.) in the individual parts of the installation are determined, inter alia, by the nature of the starting material used. In order to keep a constant operating state, despite the heterogeneous starting material, various operating parameters can be controlled.

For producing the hydrocarbons and other products in the third Fischer-Tropsch stage P3, the pressure and the temperature in the third reactor A31 are the decisive parameters. The pressure can be controlled in a short term using the compressor A42 by increasing or decreasing the performance. The temperature can in turn be controlled via the cooling performance of the heat exchanger A32. In the long term the pressure can be controlled via the pressure in the synthesis gas stream M24, on one hand by changing the operating pressure and the temperature in the second process stage, and on the other hand by controlling the cooling performance of the heat exchanger A44 and thereby the temperature and pressure drop in the synthesis gas stream M24.

The controlling a utilization installation A is comparatively simple, since the installation runs in an equilibrium with feedback, and for the control of a few relevant parameters a multiplicity of parameters, the individual operating parameters of the various installation components, can be modified, which can influence the equilibrium slowly or rapidly.

The utilization process according to the invention is preferably carried out with an elevated carbon dioxide fraction. This, inter alia, shifts the reaction equilibrium IV to the left-hand side (more carbon monoxide). The elevated operating pressure of the utilization installation between 10 and 60 bar allows such an elevated carbon dioxide content, simultaneously to a nevertheless as high as possible absolute amount of carbon monoxide, and thus of processing output. Higher or lower pressures are likewise possible, but less efficient.

The utilization installation can be optimized with respect to various aspects. For example, if mainly valuable materials such as, for example, diesel-like and petrol-like hydrocarbons and waxes, etc. are to be produced in the third process stage from carbon dioxide-neutral biomass such as, for example, woodchips, the process is directed towards an as favorable as possible ratio between the costs of the biomass and running operation and the value of the high-value materials generated. In contrast, less account needs to be taken of the emission of carbon dioxide, since it is in any case carbon dioxide-neutral biomass. In order to improve the ecological balance further, the external energy supply (electrical power etc.) can be reduced, with simultaneously elevated biomass consumption.

If, in contrast, the focus lies on an environmentally friendly disposal of polluted materials with minimum carbon dioxide production, the installation is operated in such a manner that as little carbon dioxide as possible needs to be removed from the cycle and released to the environment. This then, as the case may be, can lead to an elevated demand for external energy.

Likewise, the utilization installation can be optimized toward maximum throughput of starting material, and so as the case may be unprocessed pyrolysis coke can leave the third process stage together with the slag. The pyrolysis coke, which is environmentally little problematic, can then be landfilled together with the slag. Such a variant is advantageous for example when large amounts of polluted material need to be made harmless in a carbon-dioxide-neutral manner.

The operating temperature of the second process stage P2 can likewise be optimized. Thus, for example, the operating temperature of the second process stage P1 of the utilization unit AB can be lowered, in order to elevate the quantitative throughput in the second reactor A21. This then possibly leads to certain volatile materials in the pyrolysis gas M22 no longer being cracked and passing together with the synthesis gas M24 into the Fischer-Tropsch reactor A31. Thus, for example, benzene can pass from the starting material, for example from heavy oil, in relatively small amounts into the products of the Fischer-Tropsch synthesis. There these materials remain as part of a liquid fuel M61, but, if necessary, can also be separated off.

Figure 10:
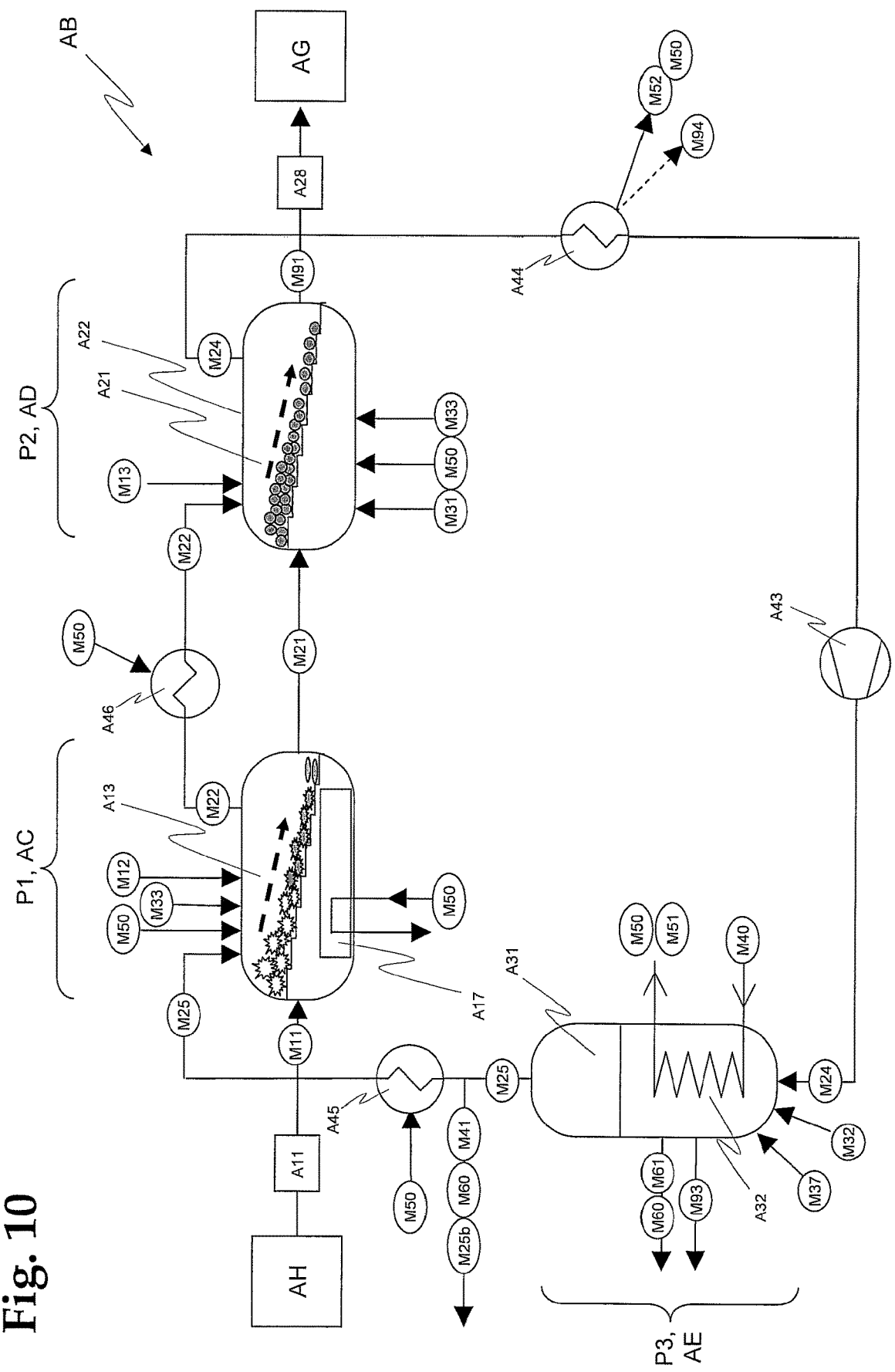

FIG. 10 schematically shows one more advantageous embodiment of a utilization unit AB. Between the first process stage P1 and the second process stage P2, a heat exchanger A46 is arranged, which serves for heating the pyrolysis gases M22 with process steam to the operating temperature of the second process stage, prior to entry into the second pressure reactor A21. It is also possible to supply the heat exchanger A46 with hot synthesis gas M24.

The compressor A43 is arranged in the transport pipe of the synthesis gas M24, downstream of a heat exchanger A44. Although the mass flow at this point of the installation is the largest, owing to the greatly lowered temperature downstream of the heat exchanger A44, the gas volume that must be handled by the compressor A43 is smaller, and the operating temperature is favorable for the compressor, since it is lower.

In the shown utilization unit AB, no cyclone separator is provided for separating off solid components M92 in the synthesis gas stream. The residual dust M92, M94 enters unhindered into the third process stage P3, where it is bound in the liquid phase of the synthesis reactor A31. Since the residual dust is insoluble in hydrocarbons, it can be filtered out without great effort. Dispensing with the cyclone separator reduces the costs of the utilization installation AB.

Figure 11:
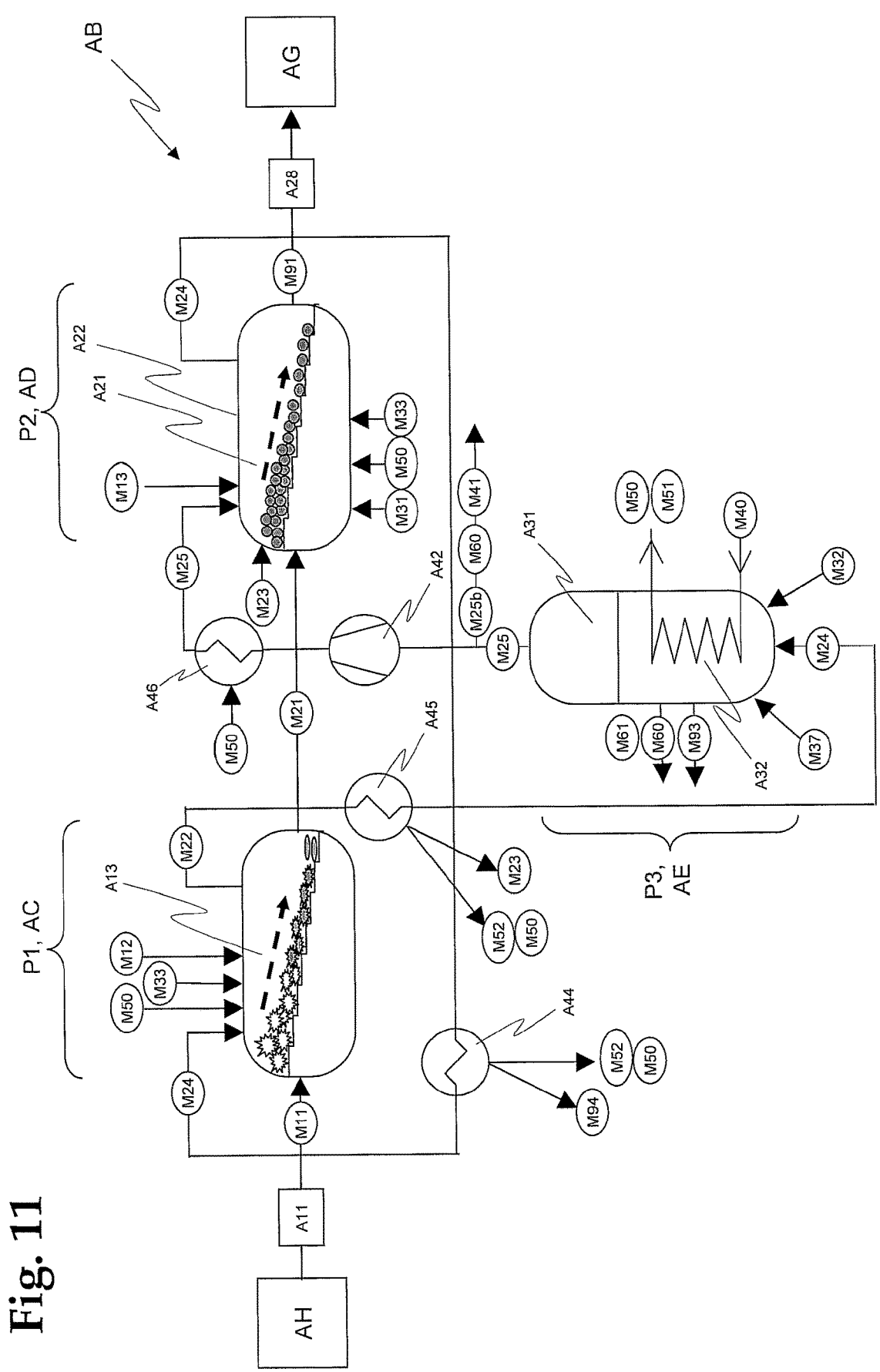

A further advantageous embodiment of a utilization unit AB of a facility Z according to the invention is shown in FIG. 11, which is particularly suitable for producing liquid fuels M61 from unpolluted biomass such as, for example, woodchips. In this variant, the pyrolysis gases M22 are not passed into the second process stage P2, but into the third process stage P3, the synthesis gas M24 is not passed into the third process stage P3, but into the first process stage P1, and the recycle gas M25 is not passed into the first process stage P1, but into the second process stage P2.

In the first process stage P1, the hot synthesis gas stream M24 heats the pyrolysis material and maintains the operating temperature. The pyrolysis gas stream M22 exiting from the first process stage, in addition to the actual pyrolysis gases, then also contains the synthesis gas fraction of the second process stage, which here thus makes a loop via the first process stage.

In the second process stage P2, the synthesis gas fraction in the pyrolysis gases M22 reacts, whereas the pyrolysis gas fractions that have not already condensed out M23 in the heat exchanger A45 dissolve in the liquid phase of the synthesis reactor A31. Since in the case of direct use of the products M60 of the third process stage as propellant or as fuel for the second drive device C11, the purity requirements are not particularly high, cracking the pyrolysis gases can be dispensed with. The propellant or fuel M61 is subsequently post-purified, in order to remove unsuitable residues such as, for example, organic acids etc. The condensed fractions M23 of the pyrolysis gas, which have a low melting point and boiling point, and contain a considerable fraction of tar, advantageously can be fed into the second process stage as solid or liquid additive M23.

The recycle gas stream M25 is subsequently compressed A42, heated A46, and passed into the second process stage P2, and so again a cycle is formed. Since cracking the gases that are introduced into the pressure reactor A21 is not necessary, the second process stage can be run at a lower operating temperature.

Figure 12:
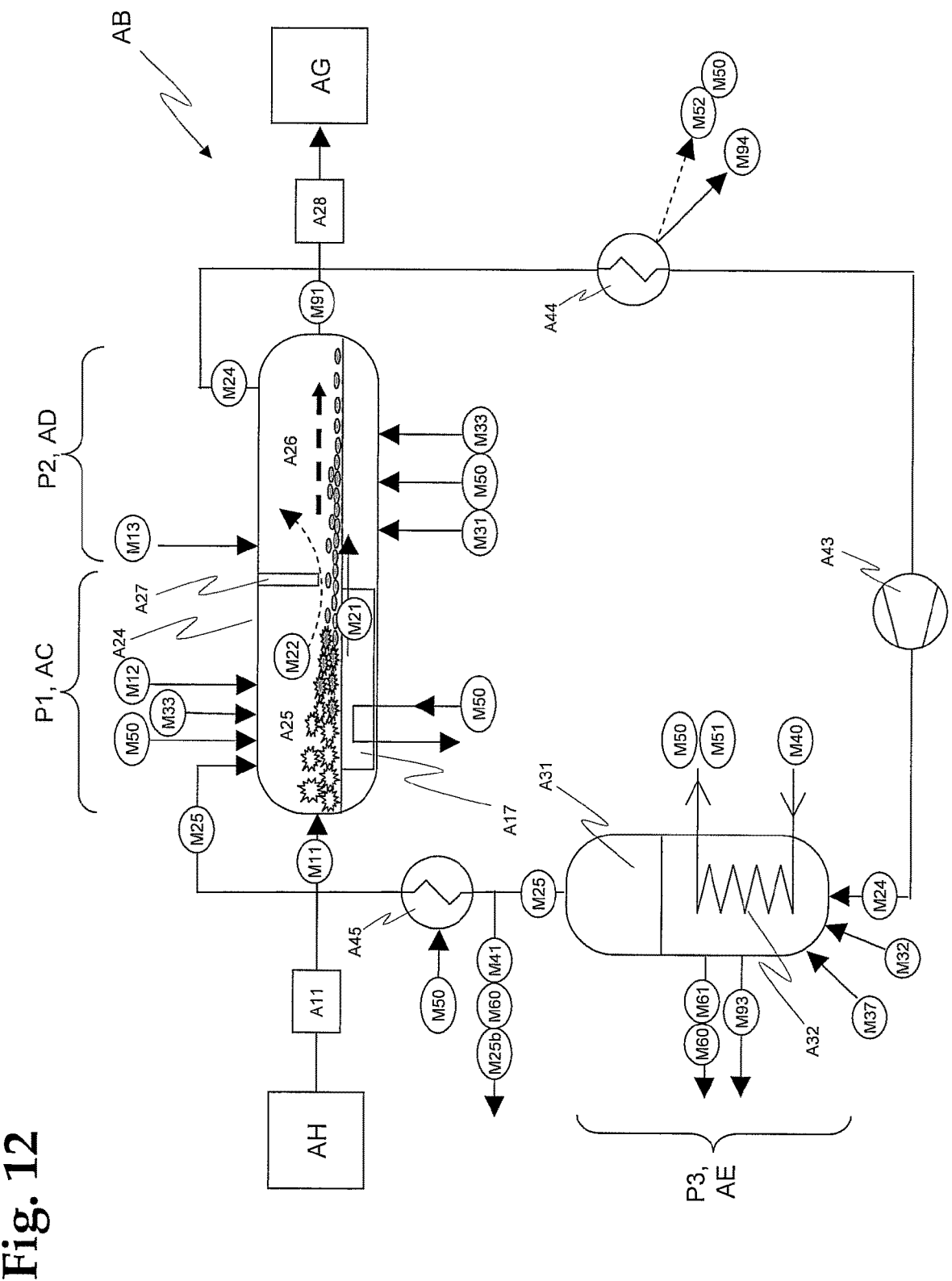

FIG. 12 shows an embodiment of a utilization unit B, in which the first process stage and the second process stage P1, P2 are carried out in a shared pressure reactor A24. The pyrolysis takes place in a first chamber A25 of the reactor A24, and the gasification in a second chamber A26. The two chambers A25, A26 are formed by a dividing wall A27 arranged in the pressure reactor A24, having a through hole through which a shared transport system conveys the pyrolysis coke M21, and through which streams the pyrolysis gas M22. The dividing wall A27 mainly serves for thermally isolating the two chambers A27, A26, such that different operating temperatures can be run in the two process stages. It is also possible to equip such a shared pressure reactor with more than one chamber.

Energy Installation for the Generation of Peak Load Energy

If a drive device C11 of an energy installation C of a facility according to the invention is configured as a combustion engine, in an advantageous variant of such a drive device water M40 can be used as an additional expansion means. For that purpose, after ignition of the combustion process, for example after self-ignition of the compressed fuel-air mixture in a Diesel engine, a certain amount of water is injected into the cylinder. This water, which is preferably finely dispersed, is subsequently vaporized by the heat energy of the exothermic oxidation reaction. So the resulting increase in gas pressure and gas volume due to the water vapor adds to the generation of the kinetic energy, wherein, however, at the same time the temperature of the overall mixture of combustion gases and water vapor is reduced. This, however, is unproblematic, or even desirable, since due to the higher energy density of a reaction with pure oxygen considerably higher reaction temperatures occur, which increases thermodynamic efficiency, but also stresses the components of the drive device C11.

Alternatively, the water can also be provided as water vapor M50. A certain amount of liquid water can also be provided mixed with the liquid fuel. At high reaction temperatures, superheated steam further acts as additional oxidation agent, in addition to the oxygen.

Hereinafter, in FIG. 13, the mode of operation of such a possible drive device C11 for a peak load energy installation C of a facility Z according to the invention will be described and explained in more detail, with reference to the example of a combustion engine in the form of a piston engine with a cylinder. Analogously, drive devices C11 that are designed as combustion engines can also be designed as turbines or Wankel engines, etc. The hot combustion gases are used in accordance with the functional principle of the respective type of combustion engine for the performance of mechanical work, for example for operating a generator installation, and in the course of that are partially expanded. Subsequently the oxidation gas M27 leaves the combustion chamber. Thus, for example in a combustion engine designed as a four-stroke piston engine, in the third stroke the combustion gas mixture M27 is ejected from the cylinder, and is subsequently compressed and cooled down. Likewise, it is possible to implement a drive device C11 as a heat engine with external combustion, for example as a steam engine or steam turbine.

Figure 13:
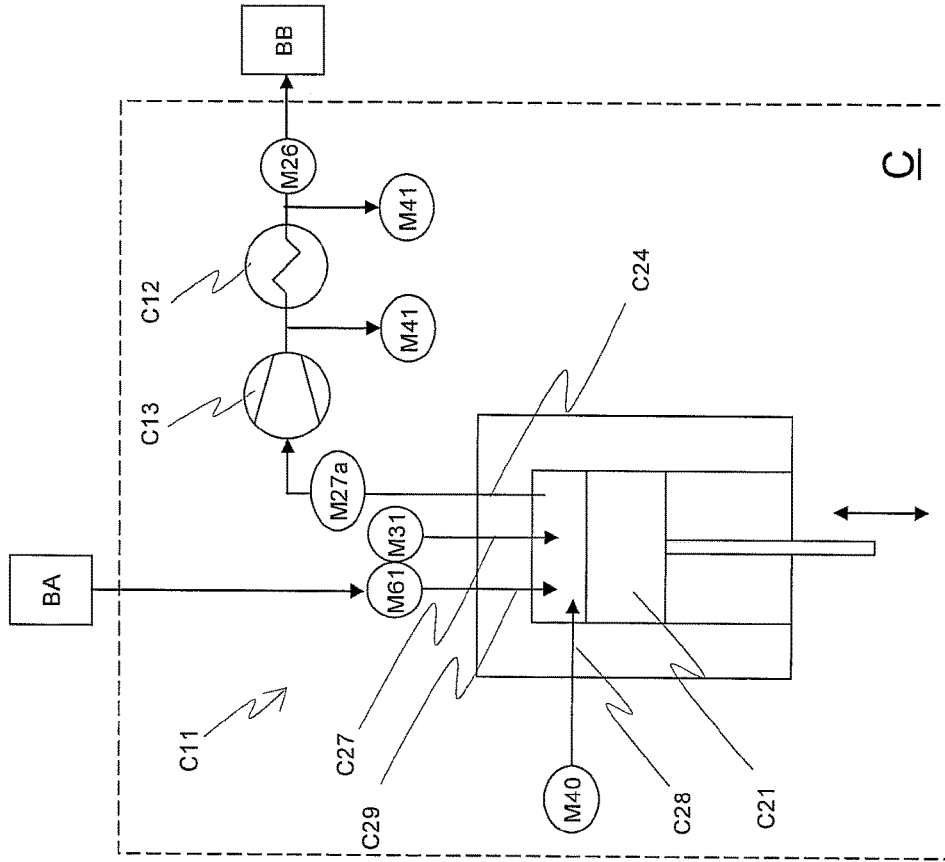
FIGS. 13 and 14 schematically show two embodiments of a drive device of a peak load energy installation, which drive device is realized as a combustion engine.

The combustion engine C11 shown in FIG. 13 comprises a cylinder C22, and a piston C23 movably arranged therein, which together form a closed combustion chamber C21. With a feed device C27 that is only schematically shown, in a first stroke oxygen M31 is introduced into the expanding combustion chamber C21. Subsequently, in a second stroke, the oxygen M31 is compressed and at the end of the second stroke the fuel M61 is introduced into the combustion chamber C21 by a feed device C29 and is combusted. In the subsequent third stroke, the expanding combustion gases M27 perform mechanical work, and during the fourth stroke the partially expanded combustion gases M27 are discharged from the combustion chamber C21 by a venting device C24, which is not shown in more detail.

The hot oxidation gases M27, which essentially consist only of carbon dioxide and water vapor, are subsequently cooled down in a downstream heat exchanger C12. The volume of these oxidation gases M27 is reduced thereby. As a result of the cooling the major part of the water M41 condenses out and is separated off. The remaining residual gas M26, which essentially consists only of carbon dioxide and possibly residual fractions of carbon monoxide and unreacted fuels, is compressed in a compressor C13 arranged in series and is collected in pressure storage BB. The condensation stage C12 upstream of the compression decreases in this process the unwanted formation of condensation water droplets in the compressor C13.

The depicted combustion engine C11 does not comprise any emissions. Since the device is not operated with air or similar gas mixtures as oxidizing agent, no air-specific pollutants such as, for example, nitrogen oxides can form either. The water formed in the combustion is not a problem and can be separated off. The carbon dioxide is conducted as residual gas M26 into the cycle of the utilization installation AB. Unburned fractions of the fuel condense out either together with the water and are separated off, or are compressed together with the carbon dioxide. The oxidation gases M27 from the drive device C11 can also be passed without cooling directly into the first or second process stage.

If the peak load energy installation C is spatially separated from the utilization installation A, and a direct return line for the residual gases M26 is not practicable, these can also be very highly compressed and transported back at high pressure in pressure storages BB from the energy installation C to the utilization installation A.

Figure 14:
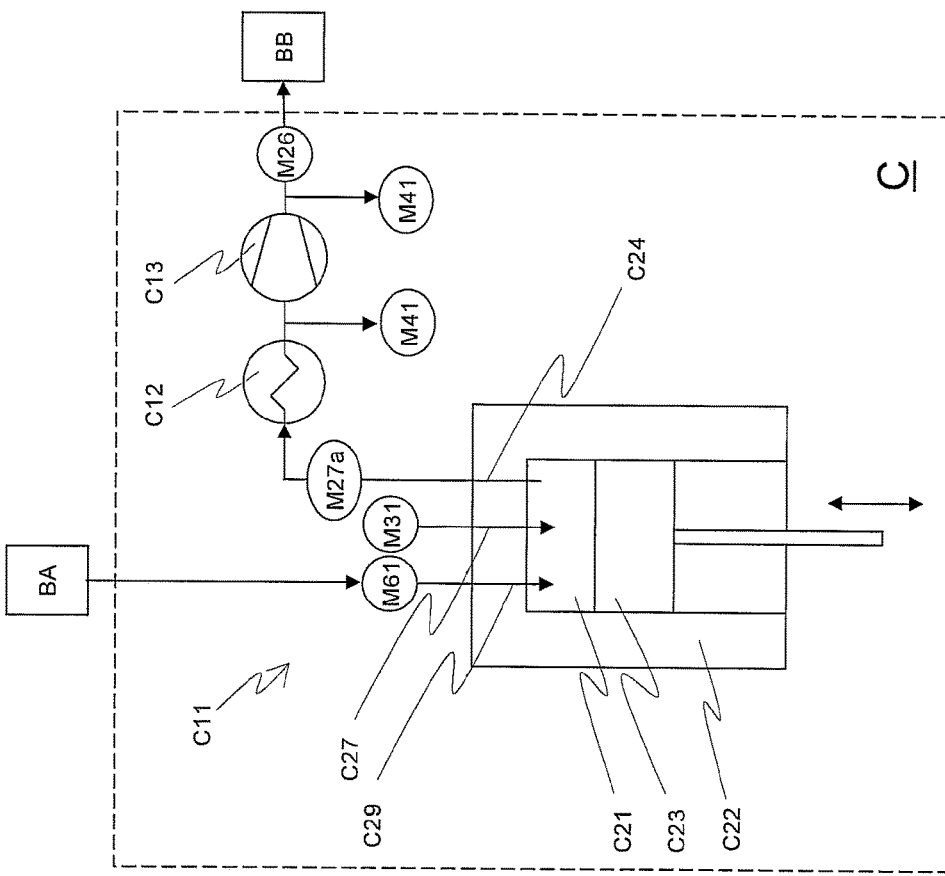

A further possible embodiment of a drive device C11 designed as a combustion engine is schematically shown in FIG. 14. In this variant water M40 is introduced into the combustion chamber C21 by means of an only schematically shown feed device C28. This proceeds preferably in such a manner that during or after the combustion reaction a defined amount of water is injected in liquid or gaseous state into the combustion chamber C21 and is finely distributed. This water is heated by the combustion heat, whereby the entire gas volume increases in the combustion chamber C21, and thereby also the gas pressure or gas volume available for performing mechanical work. Correspondingly, the amount of fuel can then be decreased, with unchanged power.

Alternatively or in addition, water M40 can also be introduced into the oxidation gas stream M27 when it leaves the combustion chamber C21. Such a variant has the advantage that the combustion reaction in the combustion chamber can proceed efficiently at temperatures as high as possible, and simultaneously the resultant temperature of the oxidation gas stream is so low that the subsequent appliances C12, C13 are less stressed.

The amount of water and the time of the injection are matched to the feed of fuel M61 and oxygen M31 in such a manner that the combustion reaction can take place efficiently. Advantageously, the resultant temperature during the oxidation reaction is essentially such that a thermodynamic efficiency of the heat engine is achieved that is as high as possible. The higher the amount of water used, the lower is in addition the relative fraction of carbon dioxide in the reaction gases, which reduces the amount of residual gas M26 remaining after condensation of the water M41.

In the embodiment shown in FIG. 14, the oxidation gases M27 are first compressed in a compressor C13 before they are subsequently cooled down in the heat exchanger C12. This variant is also combinable with the combustion engine C11 without water injection from FIG. 13, and vice versa, and can be used in general for a drive device C11.

The energy necessary for operating the compressor of a drive device C11 is advantageously generated by the drive device itself. As a consequence thereof, the achievable efficiency of the drive device decreases, but at the same time the emission-freeness of said drive device is thereby achieved. In addition, the achievable power for the same engine dimensions is greater, which again compensates for the loss of power. The compressor can, for example, be operated via a suitable gear directly by the crankshaft of a piston combustion engine.

If the drive device C11 comprises a turbine, the compressor can sit directly on the same shaft. Directly subsequent to the expansion process the oxidation gases can then be condensed and the remaining residual stream be compressed.

In another variant of a drive device, designed as a piston engine, after the combustion the oxidation gases are already precompressed within the combustion chamber in the third stroke, and are only then discharged by the venting device C24. If appropriate, the downstream compressor C13 can also be omitted.

Such an embodiment is also possible as a two-stroke variant, because in a drive device the new loading of the combustion chamber with reaction mixture (fuel M61, oxygen M31, water M40) can proceed very rapidly. In a second upward stroke, the combustion gases are precompressed, and towards the end of the stroke are released from the combustion chamber. The gaseous oxygen can be blown into the combustion chamber at high pressure at the end of the upwards stroke, since for a complete combustion reaction comparatively little oxygen is required, and water is present as additional expansion agent. The liquid fuel M61 and the water M40 as expansion agent can in any case be injected into the combustion chamber C21 very rapidly and at high pressure.

The energy consumption of the compressor C13 can be optimized by suitable combination with one or more heat exchangers or cooling elements, in which the gas volume can be reduced by disposing heat energy of the reaction gases at an internal or external heat sink.

By means of the heat exchanger/condenser C12, steam can be generated, which can either serve for increasing the efficiency of an energy unit AF of the utilization installation, or for obtaining process steam M50 for operating the utilization unit AB of the utilization installation.

Figure 15:
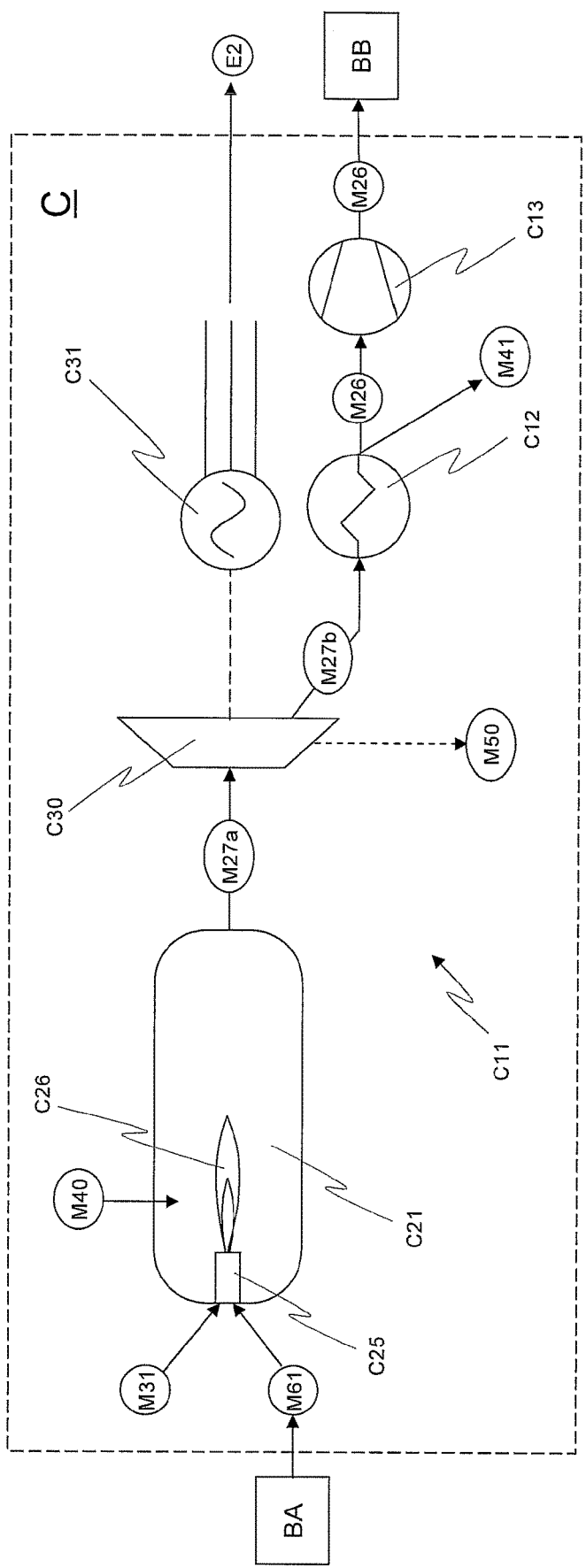
FIG. 15 schematically shows a drive device of a peak load energy installation, which drive device is realized as a combined gas/steam turbine.

FIG. 15 shows a particularly advantageous embodiment variant of a peak load energy installation C, having a drive device C11 that is constructed as a combined gas/steam turbine. In an upstream combustion chamber C21, fuel M61 is burned with oxygen M31 in a burner C25, forming a very hot combustion gas. Water is introduced into the combustion chamber C21, preferably as superheated liquid water having a temperature of, for example, 250° C., and a pressure of 50 bar. The resultant steam mixes with the combustion exhaust gases in such a manner that a hot (e.g. 600° C.) oxidation gas M27a with a high fraction of superheated steam forms, which exits from the combustion chamber C21 and is converted in a downstream turbine device C30 into mechanical work with which, in turn, a generator device C31 is driven. Depending on the design, the gas mixture in the combustion chamber behaves isochorically, in such a manner that the gas pressure increases, or isobarically, in such a manner that the gas volume increases accordingly, or both the volume and the pressure increase. Thus the following turbine device C30 must also be designed correspondingly. Suitable turbines C30 are known from the prior art, and generally have multiple process stages. In an alternative variant, partially expanded process steam M50 can be extracted downstream of a high-pressure stage of the turbine device C30, and can be used in other ways.

The expanded oxidation gas M27b is passed into a condenser/economizer C12 where the water M41 is condensed out and separated off. The remaining residual gas M26 which contains essentially carbon dioxide, is compressed in a compressor C13 and transported into the first process stage P1 of a utilization installation AB. The compressor C13 is advantageously driven directly via the turbine C30.

Instead of in the combustion chamber C21, the water M40 can also be mixed with the oxidation gas stream M27a downstream to the combustion chamber C21, for example by means of a Venturi nozzle.

In the drive device C11, the amount of water M40 and the amount of combustion mixture M61, M31, and the further chooseable parameters, are advantageously matched to one another in such a way that the downstream turbine achieves an energy utilization as high as possible. At the same time, the fraction of water in the oxidation gas mixture M27b shall be as high as possible. On one hand, this way across the condenser C12 a pressure drop as high as possible of the gas mixture is achieved, which increases the total pressure difference over the turbine C30 and thereby its efficiency. On the other hand, less residual gas M26 remains that must be compressed C13.

A further advantage of introducing steam into the combustion chamber is the cooling effect of the steam M50. The exothermic oxidation of the fuel mixture M60, M31 can lead to very high temperatures of up to 1000° C., or even 2000° C. Such temperatures would stress very much the structures of the combustion chamber C21 and of the downstream turbine device C30. The comparatively cold water vapor is preferably introduced into the chamber in such a manner that it shields the walls of the combustion chamber C21 from the very hot flame C26. The steam finally cools the entire gas mixture to 600° C. to 800° C., which lowers the thermal load of the turbine blades, and correspondingly increases the service life.

In addition to the abovementioned aspects, the drive device shown differs for example from a conventional gas turbine also in that no compressor is connected upstream of the combustion chamber. This allows a significantly simpler design of the combustion chamber C21 than in a gas turbine. Since the fuels M61 are burned with pure oxygen M31, the achievable energy density is higher than with the use of air with its reduced oxygen fraction. In order to increase the amount of oxygen that can be introduced per unit time into the combustion chamber C21, the oxygen can be pressurized in advance. The turbine device C30 can be designed like a steam turbine, since the temperature and pressure ranges of the oxidation gas M27a are essentially the same.

In normal operation, the drive device C11 of the energy installation C remains in no-load operation. A small amount of steam keeps the turbine C30 in motion, while the generator device does not produce electric power. If now the electrical power demand increases within a short time period, fuel mixture M31, M60 is injected into the combustion chamber C21 and ignited with an ignition device (not shown). At the same time, the amount of injected water M40, M50 is increased. The turbine C30 now runs up, and the generator C31 starts to operate.

The drive device C11 can also be permanently in operation, for example at 10% to 50% of the power of the base load generator installation AF. When the electrical power demand increases, the installation C can then be brought to maximum power in a very short time, for example 500% of the power of the base load generator installation AF. A facility Z according to the invention can thus adapt the total power very dynamically over a broad range. A peak load energy installation C can also have a plurality of combustion chambers C21 and/or turbine devices C30.

Modular Construction of the Installation

In a particularly advantageous embodiment of a facility according to the invention, the individual installation components are dimensioned and constructed in such a manner that they can be dismantled efficiently into individual modules, which can be transported by truck, and can subsequently be reassembled. Particularly advantageous is a maximum dimensioning of the modules that permits transport without special transport means.

Such a modular facility according to the invention has the advantage that it can also be set up only temporarily, for example for an operating time of only some years or even only months. As soon as the demand no longer exists, it can be disassembled and reconstructed at a new location. Such a facility is particularly useful, for example, in the mining industry, when in remote mining areas in a short time a relatively large energy infrastructure must be constructed, which is no longer required at the end of the mining activity. For instance, a utilization installation of a facility according to the invention can be used, for example, for producing diesel fuel from locally grown biomass and carbonaceous waste materials, for vehicles and electrical power generators of a remote open-cast mine, and/or electrical energy for operating the infrastructure.

Facilities according to the invention are particularly suitable for a modular architecture. In particular, the reactors of the first and second process stages can be constructed as horizontal reactors, having a comparatively small cross section without reducing the throughput. The reactor is simply correspondingly lengthened in the longitudinal direction. The reactor can be assembled in the longitudinal direction of a plurality of modules flanged together. The synthesis reactor may be scaled up by using a plurality of parallel reactors.

Various embodiments have been shown and described above. However, it is obvious to a person skilled in the art that various alterations and modifications can be performed without departing from the principle of the invention.

LIST OF REFERENCE SIGNS

Z Facility for the emission-free generation of energy and hydrocarbons and other products by the utilization of carbonaceous materials
A Utilization installation
AB Utilization unit
AC, AD, AE Subunits of the first, second, and third process stage of the cycle unit
A11 Pressure lock
A13 Pyrolysis reactor, first pressure reactor
A14 Pressure body
A15 Moving grate
A16, A17 Heating device
A21 Gasification reactor, second pressure reactor
A22 Pressure body
A23 Moving grate
A24 Shared pressure reactor of first and second process stage
A25 First chamber
A26 Second chamber
A27 Dividing wall
A28 Pressure lock
A31 Fischer-Tropsch reactor, synthesis reactor
A32 Synthesis stage cooling, boiler in the steam cycle of the energy unit AF
A41, A42, A43 Compressor
A44, A45, A46 Heat exchanger, superheater of the steam cycle of energy unit AF
A47 Cyclone separator
A48 Pressure reduction
A49, A50, A51, A52 Shut-off valve
A53 Non-return valve
AF Energy unit of the utilization installation, installation component for the emission-free generation of base load energy
A61 Drive device
A62 Steam turbine
A63 Condenser, economizer
A64 Generator device
A65 External cooling cycle
A66 Pump
AG Discharging unit, installation component for discharging and treating ash and residual materials
A91 Silo, storage container
AH Treatment unit, installation component for treating and supplying carbonaceous material
A92 slag depot B installation for transport and temporary storage of fuels and oxidation gases between utilization installation and energy installation
BA Fuel storage unit
BB Oxidation gas storage unit
BC Ship, train, pipeline, transport means
C Energy installation, installation component for the emission-free generation of peak load energy by utilizing the carbonaceous fuels from the utilization installation
C11 Drive device
C12 Condenser/economizer
C13 Compressor
C14 External cooling cycle
C21 Combustion chamber
C22 Cylinder
C23 Piston
C24 Venting device
C25 Burner
C26 Flame
C27 Feed device for oxygen
C28 Feed device for water
C29 Feed device for fuel
C30 Turbine
C31 Generator device
D Installation for the generation and supply of external chemical energy, installation component for the production of hydrogen
DA Wind power unit
DB Solar energy unit
DC Electrolysis unit
DD hydrogen producing industry
DE temporary storage unit
DF temporary storage unit
DG Ship, train, pipeline, transport means
E1 electrical/mechanical energy (base load)
E2 electrical/mechanical energy (peak load)
E3 supplied electrical energy
E4 thermal energy
P1 First stage of process
P2 Second stage of process
P3 Third stage of process
P6 Intake of the carbonaceous materials
P7 Discharge of the residues
M10 Untreated carbonaceous starting material
M11, M12 Carbonaceous starting material
M13 Additional combustibles
M14 Additional fuel
M17 sorted residual materials, recycling material
M21 Pyrolysis coke
M22 Pyrolysis gas
M23 Low-volatility fractions of the pyrolysis gas
M24, M24$a$, M24$b$ Synthesis gas
M25, M25$a$, M25$b$ Recycle gas
M26 Residual gas
M27, M27$a$, M27$b$ Oxidation gases
M31 Oxygen, oxidizing agent
M32 Hydrogen gas
M33 Carbon dioxide
M37 Catalyst
M40 Water, process water, feed water
M41 Condensate, condensed water
M50 Process steam
M51, M52, M53, Steam in the turbine cycle
M60 Products of the synthesis stage
M61 Products of the synthesis stage, fuel
M90 Residues
M91 Slag, ash, residues
M92 Residual dust
M93 Residues
M94 Graphite, activated carbon, carbonaceous residues
t Time
P Power
$P_a$ Heat content
$P_b$ Thermal power of a conventional power station
$P_c$, $P_{c1}$, $P_{c2}$ Base load power
$P_d$ Effective thermal power of a facility according to the invention
$P_e$, $P_{e1}$, $P_{e2}$ Total power
$P_f$ Base load power of the base load energy unit
$P_g$ Fuel production power of the utilization installation

What is claimed is:

1. A process for the emission-free generation of energy and/or hydrocarbons and other products by utilization of carbonaceous materials, comprising:
in a first process stage, supplying the carbonaceous materials to a first subunit,
pyrolyzing the carbonaceous materials in the first subunit to form pyrolysis coke and pyrolysis gas, wherein the pyrolysis coke is lying on a conveying means adapted for continuous horizontal transport of lumpy pyrolysis coke along a horizontal direction, and
passing the pyrolysis coke and the pyrolysis gas into a second subunit;
in a second process stage, gasifying in the second subunit the pyrolysis coke from the first process stage in a fire bed that is formed by pyrolysis coke lying on a conveying means adapted for continuous horizontal transport of lumpy pyrolysis coke along a horizontal direction, at a temperature above 850° C., to form synthesis gas and slag and other residues, wherein a point of entry of the pyrolysis gas into the second subunit is above the fire bed of the pyrolysis coke, and wherein oxygen is blown into the fire bed, spatially separated from the point of entry of the pyrolysis gas, such that the pyrolysis gas does not come into contact with oxygen,
removing said slag and other residues, and
passing the synthesis gas into a third subunit;
in a third process stage, converting in the third subunit the synthesis gas from the second process stage into hydrocarbons and/or other solid, liquid and/or gaseous products, and a recycle gas comprising carbon dioxide, water vapor, and unreacted carbon monoxide and hydrogen, by using Fischer-Tropsch-synthesis and/or liquid phase methanol synthesis,
discharging said products, and
passing the recycle gas into the first subunit,
thereby forming an essentially closed cycle from the first process stage to the second process stage to the third process stage and back to the first process stage.

2. The process according to claim 1, wherein hydrogen is supplied in at least one said process stage.

3. The process according to claim 1, wherein carbon dioxide is supplied in at least one said process stage.

4. The process according to claim 1, wherein there is a pressure drop along the cycle.

5. The process according to claim 1, wherein heat energy for the pyrolysis reactions in the first process stage is provided, at least in part by returning a part of hot synthesis gas from the second process stage into the first process stage, and/or by partial oxidation of the carbonaceous starting material and the resultant pyrolysis coke.

6. The process according to claim 1, wherein the first process stage is carried out at a temperature between 300° C. and 800° C.

7. The process according to claim 1, wherein for the gasification reaction in the second process stage oxygen and/or steam and/or carbon dioxide is used as a gasification agent.

8. The process according to claim 1, wherein in the second process stage, the thermal energy required for the gasification reaction is supplied, at least in part from outside;
and/or is generated by oxidizing a part of the pyrolysis coke with an oxidizing agent.

9. The process according to claim 1, wherein the second process stage is carried out at a temperature between 850° C. and 1600° C.

10. The process according to claim 1, wherein the first process stage and/or the second process stage is carried out at a pressure between 1 and 60 bar.

11. The process according to claim 1, wherein the first process stage and the second process stage are carried out in a pressure reactor and wherein the same pressure reactor is used to carry out both the first and the second process stages.

12. The process according to claim 1, wherein electrical and/or mechanical energy is generated by oxidation of the hydrocarbons and other solid, liquid, and/or gaseous products of the third process stage, to an oxidation gas, said oxidation gas consisting essentially of carbon dioxide and water.

13. The process according to claim 12, wherein pure oxygen is used as an oxidizing agent.

14. The process according to claim 12, wherein water is condensed out and/or separated from the oxidation gas.

15. The process according to claim 12, wherein at least a part of the oxidation gas is fed back into at least one of the first process stage, the second process stage and the third process stage of the generation process.

16. The process according to claim 1, wherein electrical and/or mechanical energy is generated by cooling the synthesis gas in a heat exchanger, wherein superheated steam and/or another hot gas are formed, from which electrical and/or mechanical energy is generated using a heat engine.

17. The process according to claim 2, wherein the hydrogen is supplied in the third process stage.

18. The process according to claim 3, wherein the carbon dioxide is supplied in the first process stage or the second process stage.

19. The process according to claim 6, wherein the first process stage is carried out at a temperature between 450° C. and 700° C.

20. The process according to claim 6, wherein the first process stage is carried out at a temperature between 500° C. and 600° C.

21. The process according to claim 8, wherein the thermal energy required for the gasification reaction in the second process stage is supplied by heating devices and/or heat exchangers.

22. The process according to claim 8, wherein the thermal energy required for the gasification reaction is generated by oxidizing a part of the pyrolysis coke using oxygen as the oxidizing agent.

23. The process according to claim 9, wherein the second process stage is carried out at a temperature between 850° C. and 1400° C.

24. The process according to claim 9, wherein the second process stage is carried out at a temperature between 850° C. and 1000° C.

25. The process according to claim 10, wherein the pressure is between 5 bar and 25 bar.

26. The process according to claim 10, wherein the pressure is between 10 bar and 15 bar.

27. The process according to claim 16, wherein the heat engine is a steam turbine.

* * * * *